United States Patent
Tanaka et al.

(10) Patent No.: US 10,980,559 B2
(45) Date of Patent: Apr. 20, 2021

(54) TREATMENT INSTRUMENT

(71) Applicant: OLYMPUS CORPORATION, Hachioji (JP)

(72) Inventors: Kazuhiro Tanaka, Hachioji (JP); Yusuke Takei, Hino (JP); Ojiro Kitamura, Hachioji (JP); Akinori Kobayashi, Hino (JP); Tatsuro Yamamoto, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 212 days.

(21) Appl. No.: 16/208,943

(22) Filed: Dec. 4, 2018

(65) Prior Publication Data

US 2019/0117246 A1    Apr. 25, 2019

Related U.S. Application Data

(63) Continuation of application No. PCT/JP2016/066288, filed on Jun. 20, 2016.

(51) Int. Cl.
*A61B 17/29* (2006.01)
*A61B 17/32* (2006.01)
(Continued)

(52) U.S. Cl.
CPC ...... *A61B 17/29* (2013.01); *A61B 17/320092* (2013.01); *A61B 18/085* (2013.01);
(Continued)

(58) Field of Classification Search
CPC ............ A61B 17/29; A61B 17/320092; A61B 2017/00314; A61B 2017/00331;
(Continued)

(56) References Cited

U.S. PATENT DOCUMENTS

| 5,383,888 A | 1/1995 | Zvenyatsky et al. |
| 5,849,022 A * | 12/1998 | Sakashita ............... A61B 17/29 606/174 |

(Continued)

FOREIGN PATENT DOCUMENTS

| JP | 2008-18233 A | 1/2008 |
| JP | 2013-81779 A | 5/2013 |
| JP | 2013-176651 A | 9/2013 |

OTHER PUBLICATIONS

Sep. 20, 2016 International Search Report issued in International Patent Application No. PCT/JP2016/068288.
(Continued)

*Primary Examiner* — Kathleen S Holwerda
(74) *Attorney, Agent, or Firm* — Oliff PLC

(57) ABSTRACT

In a treatment instrument, one of a pair of jaws is supported by a supporter while being pivot able around the supporter with respect to the supporter. A drive member moves along a longitudinal axis so that the pair of the jaws are closed with respect to each other, thereby applying an axial force onto an elongated member from the drive member by way of the one of the jaws and the supporter in a direction along the longitudinal axis. A contact surface of the elongated member abuts on a housing when the elongated member moves with respect to the housing under the axial force, thereby suppressing rotation of the elongated member around the longitudinal axis with respect to the housing.

11 Claims, 13 Drawing Sheets

(51) Int. Cl.
*A61B 18/14* (2006.01)
*A61B 18/08* (2006.01)
*A61B 17/00* (2006.01)
*A61B 18/00* (2006.01)

(52) U.S. Cl.
CPC ...... *A61B 18/1442* (2013.01); *A61B 18/1445* (2013.01); *A61B 2017/00314* (2013.01); *A61B 2017/00331* (2013.01); *A61B 2017/293* (2013.01); *A61B 2017/294* (2013.01); *A61B 2017/2919* (2013.01); *A61B 2017/2925* (2013.01); *A61B 2017/2927* (2013.01); *A61B 2017/2929* (2013.01); *A61B 2017/2936* (2013.01); *A61B 2017/2946* (2013.01); *A61B 2018/00202* (2013.01)

(58) Field of Classification Search
CPC .... A61B 2017/2919; A61B 2017/2925; A61B 2017/2927; A61B 2017/2929; A61B 2017/293; A61B 2017/2936; A61B 2017/294; A61B 2017/2946; A61B 17/068–17/076; A61B 17/115–2017/1157; A61B 18/1442; A61B 18/1445; A61B 18/1447; A61B 2018/00202
See application file for complete search history.

(56) References Cited

U.S. PATENT DOCUMENTS

| | | | | |
|---|---|---|---|---|
| 5,893,835 | A | * | 4/1999 | Witt ............... A61B 17/320092 601/2 |
| 2008/0061108 | A1 | * | 3/2008 | Scirica ............. A61B 17/07207 227/175.1 |
| 2008/0314954 | A1 | * | 12/2008 | Boudreaux ...... A61B 17/07207 227/175.1 |

OTHER PUBLICATIONS

Oct. 8, 2019 Office Action issued in Japanese Patent Application No. 2018-523177.
Oct. 27, 2020 Office Action issued in Chinese Patent Application No. 201680086739.6.

* cited by examiner

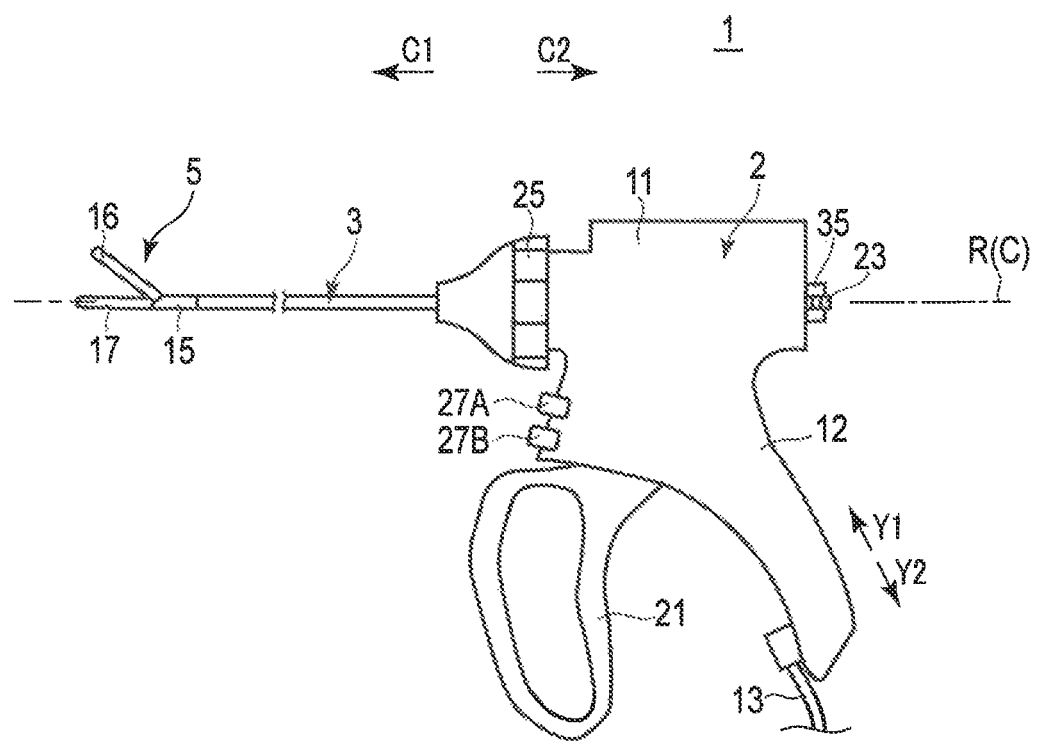
F I G. 1
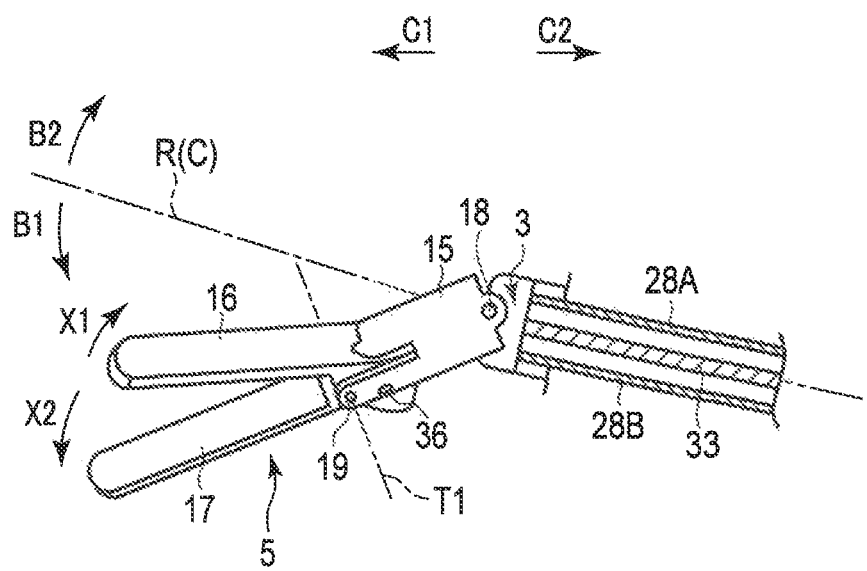
F I G. 2

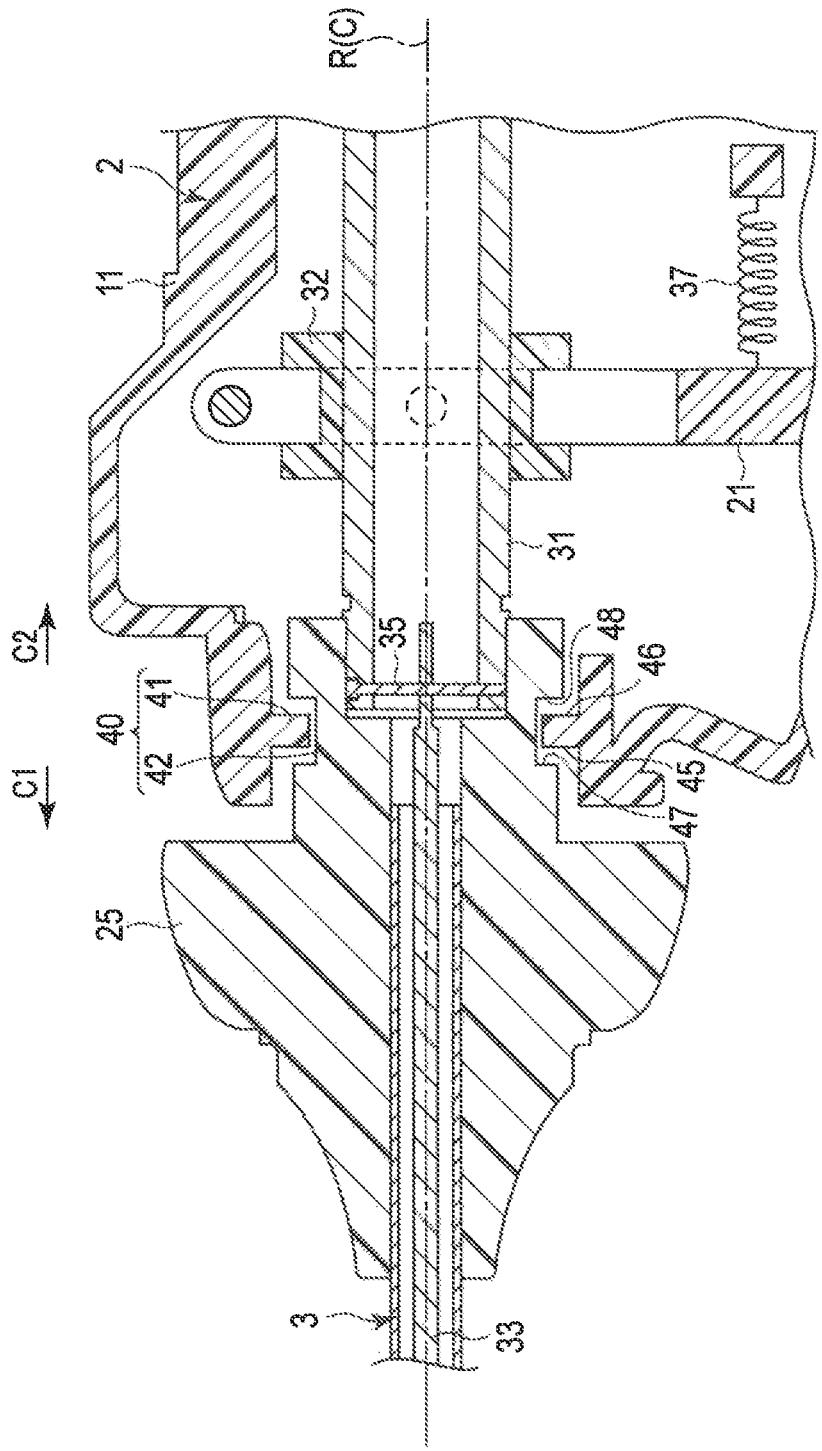
F I G. 3

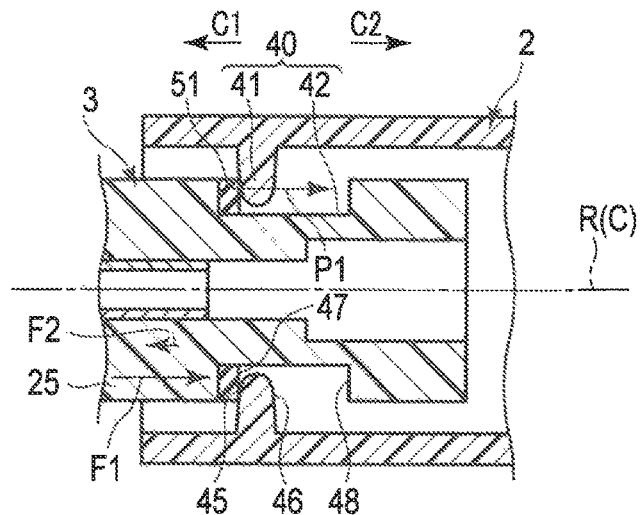
F I G. 8
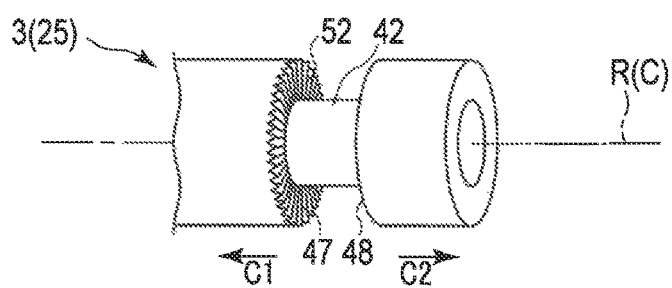
F I G. 9
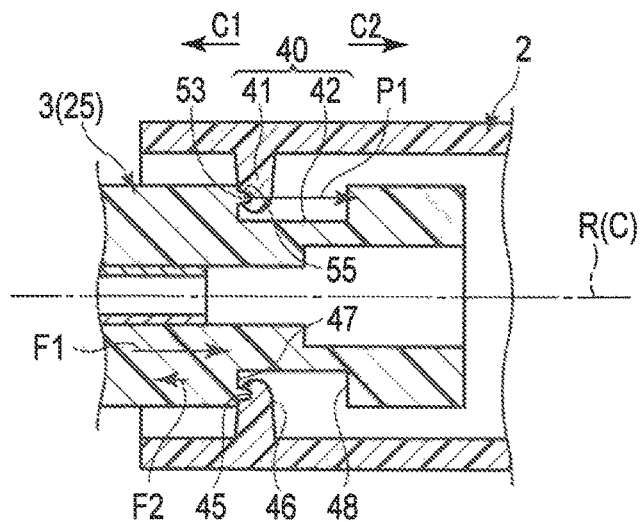
F I G. 10

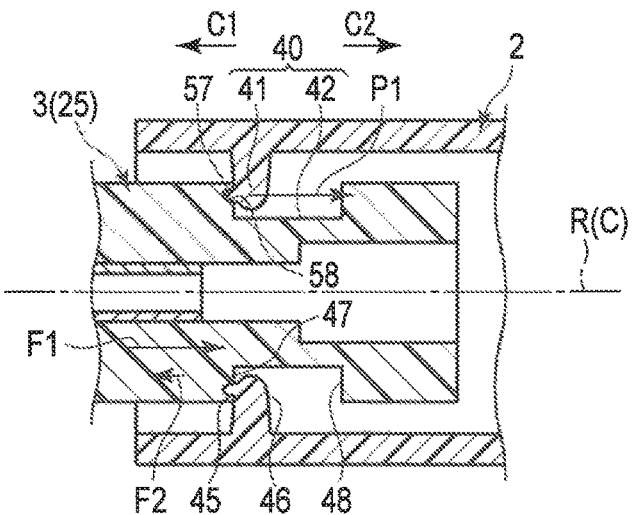
F I G. 11
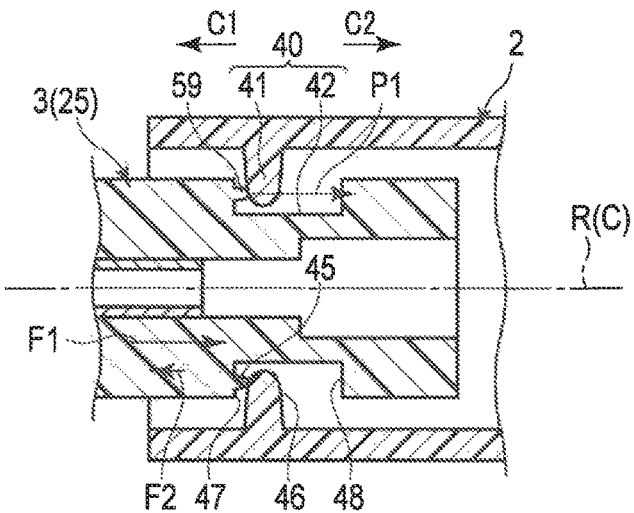
F I G. 12
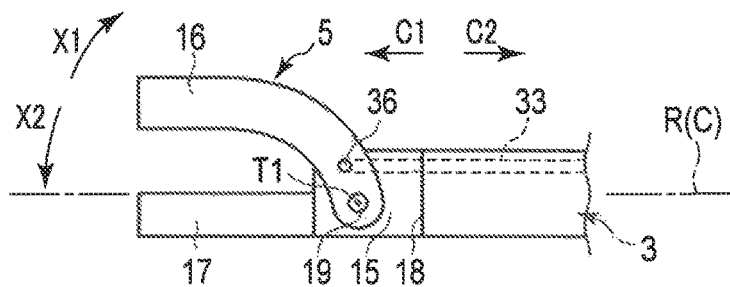
F I G. 13

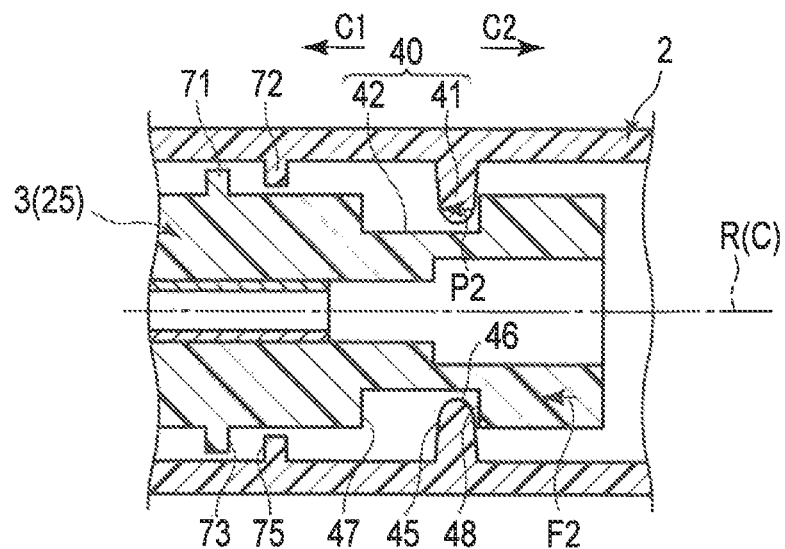
F I G. 18
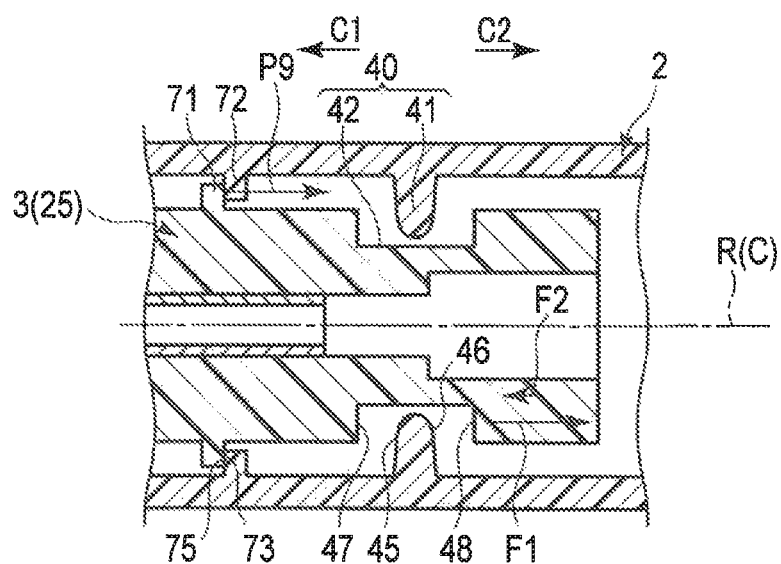
F I G. 19

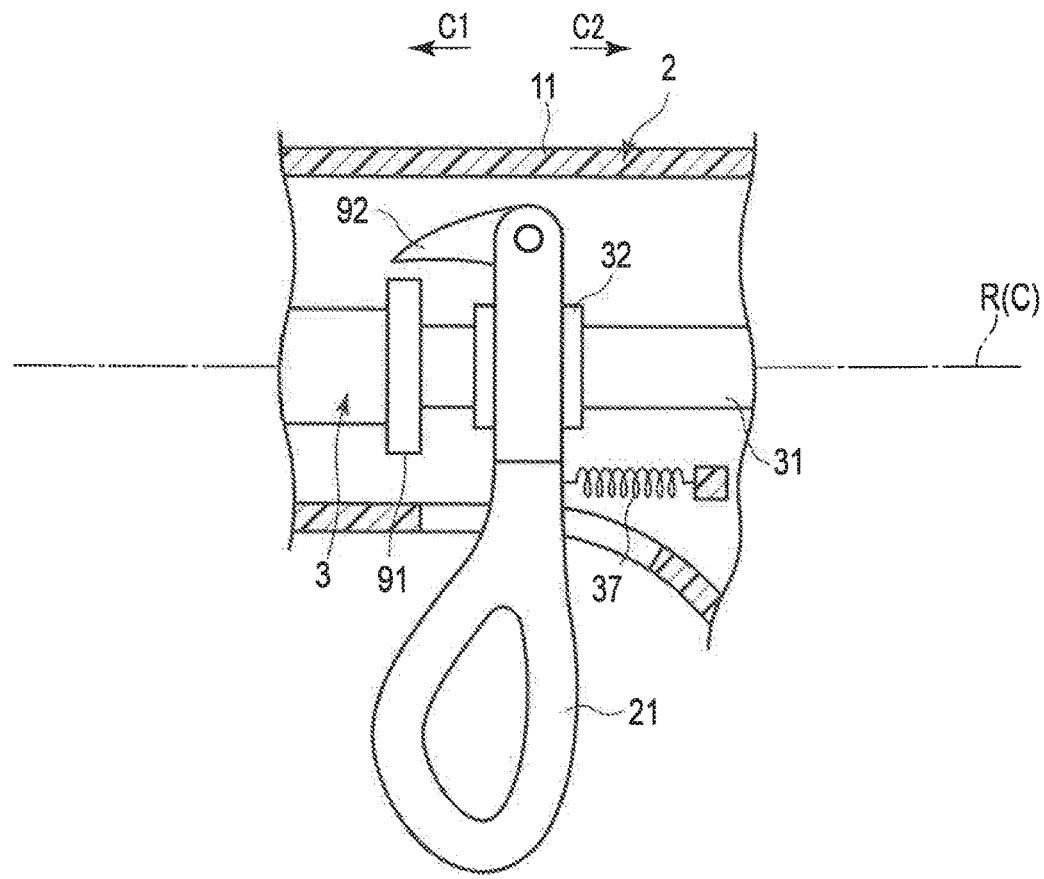
F I G. 23
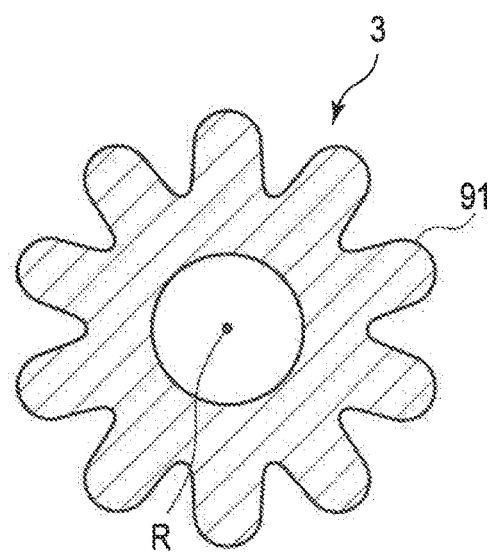
F I G. 24

TREATMENT INSTRUMENT

CROSS-REFERENCE TO RELATED APPLICATIONS

This is a Continuation Application of PCT Application No. PCT/JP2016/068288, filed Jun. 20, 2016, the entire contents of which are incorporated herein by reference.

BACKGROUND OF THE INVENTION

1. Field of the Invention

The present invention relates to a treatment instrument for treating a treatment target with an end effector.

2. Description of the Related Art

The specification of U.S. Pat. No. 5,383,888 discloses a treatment instrument provided with an end effector for treating a treatment target, the end effector being provided on the distal portion of a shaft. In this treatment instrument, the shaft is coupled to a housing that can be gripped by a user, and by opening or closing the handle with respect to the grip of the housing, a pair of gripping pieces of the end effector open and close with respect to each other. By closing the gripping pieces, the treatment target such as living body tissue can be held between the gripping pieces. A rotating member (rotating knob) is attached as part of the shaft to the housing in a manner rotatable around the center axis of the shaft. When an operation force for rotating the rotating member is applied, the shaft and the end effector rotate together with the rotating member with respect to the housing, with the center axis of the shaft serving as a reference rotation axis. In this manner, the angular position of the end effector around the reference rotation axis changes. Furthermore, the end effector of this treatment instrument bends with respect to the shaft (the center axis of the shaft) in accordance with an operation performed by the bending operation section (wing member), which is provided in the housing.

BRIEF SUMMARY OF THE INVENTION

According to one aspect of the invention, a treatment instrument includes that: an end effector including a first jaw, a second jaw, and a supporter, the supporter pivotally supporting the first jaw, and the first jaw and the second jaw being opened or closed with respect to each other in accordance with pivoting of the first jaw around the supporter with respect to the supporter; an elongated member having a longitudinal axis, the end effector being attached at a distal end of the elongated member; a housing including an operation input member, an operation of opening or closing the end effector being input with the operation input member, and the elongated member being attached to the housing in a state in which the elongated member is rotatable together with the end effector around the longitudinal axis; a drive member having a distal end connected to the first jaw, the drive member being configured to move along the longitudinal axis of the elongated member based on the operation input with the operation input member so that the first jaw pivots around the support portion, and thereby being configured to close the first jaw and the second jaw with respect to each other in accordance with the pivoting of the first jaw so that the drive member applies a first axial force onto the elongated member by way of the first jaw and the supporter in a direction along the longitudinal axis; and a first contact surface provided on the elongated member, the first contact surface being configured to abut on the housing when the elongated member moves along the longitudinal axis with respect to the housing under the first axial force, thereby suppressing rotation of the elongated member around the longitudinal axis with respect to the housing.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic diagram showing a treatment instrument according to a first embodiment;

FIG. 2 is a perspective view schematically showing the configuration of an end effector according to the first embodiment;

FIG. 3 is a cross-sectional view schematically showing the internal configuration of a housing according to the first embodiment;

FIG. 8 is a cross-sectional view schematically showing the joint between the shaft and the housing, with the gripping pieces being in the closed state according to a second modification;

FIG. 9 is a perspective view schematically showing an engagement recess of the shaft according to a third modification;

FIG. 10 is a cross-sectional view schematically showing the joint between the shaft and the housing, with the gripping pieces being in the closed state according to a fourth modification;

FIG. 11 is a cross-sectional view schematically showing the joint between the shaft and the housing, with the gripping pieces being in the closed state according to a fifth modification;

FIG. 12 is a cross-sectional view schematically showing the joint between the shaft and the housing, with the gripping pieces being in the closed state according to a sixth modification;

FIG. 13 is a schematic diagram showing the configuration of the end effector according to a seventh modification;

FIG. 18 is a cross-sectional view schematically showing the joint between the shaft and the housing and near the joint, with the gripping pieces being in the open state according to a ninth modification;

FIG. 19 is a sectional view schematically showing the joint between the shaft and the housing and near the joint, with the gripping pieces being in the closed state according to the ninth modification;

FIG. 23 is a schematic diagram showing the internal configuration of the housing according to a first reference example;

FIG. 24 is a cross-sectional view schematically showing the shaft according to the first reference example, taken in a cross section which is approximately perpendicular to the reference rotation axis and which passes through the gear.

DETAILED DESCRIPTION OF THE INVENTION

First Embodiment

Figure 4:
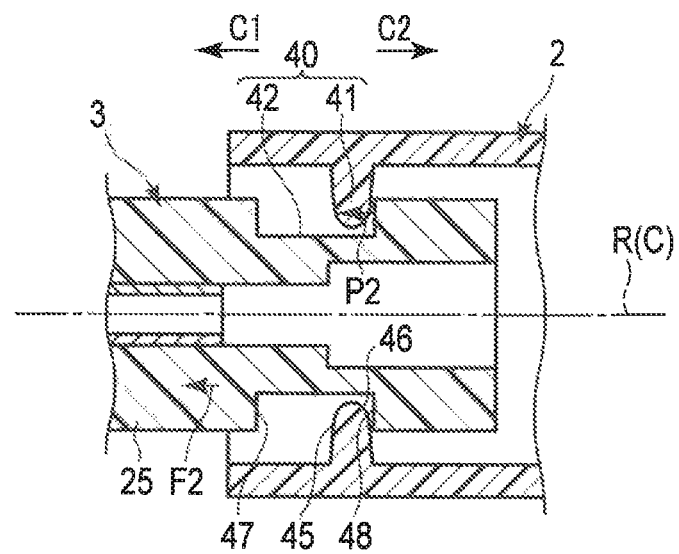
FIG. 4 is a cross-sectional view schematically showing a joint between a shaft and the housing, with gripping pieces being in an open state according to the first embodiment.

A first embodiment of the present invention will be described with reference to FIGS. 1 to 5. FIG. 1 is a diagram showing a treatment instrument (gripping treatment instrument) 1 according to the present embodiment. As shown in FIG. 1, the treatment instrument 1 has a longitudinal axis C. Here, one side in the direction along the longitudinal axis C is defined as a distal side (arrow C1 side), and the other side that is opposite to the distal side is defined as a proximal side (arrow C2 side).

The treatment instrument 1 includes a housing 2 that can be gripped, a shaft (sheath) 3 coupled to the distal side of the housing 2, and an end effector 5 attached to the distal portion of the shaft (elongated member) 3. The shaft 3 extends along the longitudinal axis C from the proximal side to the distal side, and the center axis of the shaft 3 is approximately coaxial with the longitudinal axis C. In the shaft 3, the side toward the housing 2 is the proximal side, and the side toward the end effector 5 is the distal side. The shaft 3 is rotatable around its center axis with respect to the housing 2. That is, the center axis of the shaft 3 serves as the reference rotation axis R of the rotation of the shaft 3 with respect to the housing 2.

The housing 2 includes a housing main body 11 extending along the longitudinal axis C (rotation axis R of the shaft 3), and a grip (stationary handle) 12 extending from the housing main body 11 along a direction. (arrows Y1 and Y2) that intersects the reference rotation axis R. The grip 12 is provided at a position away from the reference rotation axis R (longitudinal axis C). A cable 13, at one end thereof, is connected to the grip 12. The other end of the cable 13 is connected to an energy control device (not shown). Here, the direction intersecting (approximately perpendicular to) the longitudinal axis C (reference rotation axis R) and also intersecting (approximately perpendicular to) the extension direction of the grip 12 is defined as the width direction of the housing 2 (direction approximately perpendicular to the sheet of FIG. 1). FIG. 1 is a diagram of the treatment instrument 1 viewed from one side of the housing 2 in its width direction.

FIG. 2 shows the configuration of the end effector 5. As shown in FIGS. 1 and 2, the end effector 5 is rotatable together with the shaft 3 around the reference rotation axis R with respect to the housing 2, and is also bendable with respect to the shaft 3 (reference rotation axis R). With the rotation of the end effector 5, the angular position of the end effector 5 around the reference rotation axis R changes. The bending direction of the end effector 5 (direction indicated by arrows B1 and B2) intersects (approximately perpendicular to) the reference rotation axis R. The end effector 5 is provided with an intermediary member 15, a first gripping piece 16, and a second gripping piece 17. The intermediary member 15 is mounted at the distal end of the shaft 3 in a bendable manner with respect to the shaft 3. That is, a bending joint 18 is provided between the shaft 3 and the intermediary member 15. The pair of gripping pieces 16 and 17 of the end effector 5 openable and closable with respect to each other. The opening and closing direction of the gripping pieces 16 and 17 (the direction indicated by arrows X1 and X2) intersects the reference rotation axis R, and also intersects the bending direction of the end effector 5.

The first gripping piece 16, which is a first jaw, is attached to the intermediary member 15 by way of a support pin (support portion) 19, the first gripping piece being pivot able with respect to the intermediary member 15 and the support pin 19. That is, the intermediary member 15 is provided with the support pin 19 to support the first gripping piece 16. The first gripping piece 16 can pivot around the support pin 19. According to the present embodiment, the rotation axis T1 of the first gripping piece 16 with respect to the intermediary member 15 runs through the support pin 19, and is approximately coaxial with the center axis of the support pin 19. The rotation axis T1 extends approximately in parallel with the bending direction of the end effector 5. That is, the extending direction of the rotation axis T1 intersects the reference rotation axis R, and also intersects with the opening and closing directions of the gripping pieces 16 and 17. In accordance with the pivoting of the first gripping piece 16 around the support pin (support portion) 19, the first gripping piece 16 opens or closes with respect to the second gripping piece 17. Furthermore, the support pin (supporter) 19 is rotatable together with the shaft 3 and the end effector 5 around the reference rotation axis R with respect to the housing 2.

Here, in one example, the second gripping piece 17, which is the second jaw, may be fixed to the intermediary member 15 or formed integrally with the intermediary member 15. In another example, the second gripping piece 17 may also be pivotally attached to the intermediary member 15. In yet another embodiment, a rod member (not shown) may extend from the inside of the intermediary member 15 toward the distal side so that the projecting portion of the rod member from the intermediary member 15 toward the distal side can form the second gripping piece 17.

A handle (movable handle) 21 is pivotally attached to the housing 2. The handle 21, which is an opening/closing operation input member, pivots with respect to the housing 2 so that the handle 21 opens and closes with respect to the grip 12. That is, the handle 21 is configured to open and close with respect to the grip 12. In this embodiment, because the treatment instrument 1 is a gun shape type, the handle 21 is positioned on the side where the grip 12 is arranged with respect to the reference rotation axis R (longitudinal axis C) and on the distal side with respect to the grip 12. The moving direction of the handle 21 in the opening movement and the closing movement with respect to the grip 12 is approximately parallel to the longitudinal axis C. An example may be such that the handle 21 is provided on the proximal side with respect to the grip 12. In another example, the handle 21 and the grip 12 may be provided on the opposite sides with respect to each other with the reference rotation axis R being a center, and the movement direction of the handle 21 with respect to the grip 12 in the opening and closing movements may be approximately perpendicular to the longitudinal axis C.

A bend dial 23 is attached as a bending operation input section (operation input member) to the housing 2. For example, by rotating the bend dial 23, the operation of bending the end effector 5 with respect to the shaft 3 is input. As shown in FIG. 2, bend drive members 28A and 28B, such as wires or flat springs, extend along the reference rotation axis R (longitudinal axis C) inside the shaft 3. The distal ends (one side ends) of the bend drive members 28A and 28B are connected to the intermediary member 15 of the end effector 5. Furthermore, the proximal ends of the bend drive members 28A and 28B are connected mechanically to the bend dial 23 by way of a pulley (not shown) or the like which is provided inside the housing 2. An operation is input from the bending dial (bending operation input member) 23 so that the operation force is transmitted to the bend drive members 28A and 28B. The bend drive members 28A and 28B are thereby moved along the longitudinal axis C (reference rotation axis R) with respect to the shaft 3 and the housing 2. As a result, the end effector 5 bends with respect to the shaft 3 (reference rotation axis R) in the bending direction (direction indicated by arrow B1 and arrow B2).

Here, the bend drive members 28A and 28B are rotatable together with the shaft 3 and the end effector 5 around the reference rotation axis R with respect to the housing 2. The bend dial 23 may also be rotatable together with the shaft 3 and the end effector 5 around the reference rotation axis R with respect to the housing 2, or may not be rotatable around the reference rotation axis R together with the shaft 3 and the end effector 5. In this embodiment, the bend dial 23 is attached to the proximal end surface of the housing main body 11, but the bend dial 23 does not always have to be provided at this position. For example, a bending operation input section such as a bend dial (23) may be attached to the outer surface of the housing main body 11 that faces opposite side of the side on which the grip 12 is located with respect to the reference rotation axis R (longitudinal axis C).

A rotating member (rotating knob) 25, which is part of the shaft 3, is attached to the distal side of the housing main body 11. The shaft 3 is inserted into the housing main body 11 from the distal side, and attached to the housing 2. The rotation member 2 is fixed to the shaft 3, and rotates together with the shaft 3 and the end effector 5 around the reference rotation axis R with respect to the housing 2. In the present embodiment, an operation force for rotating the shaft 3 and the end effector 5 (support pin 19) around the reference rotation axis R is applied to the rotation member 25, which is the rotational operation input member.

Furthermore, operation buttons 27A and 27B are attached to the housing 2. When the operation button 27A or 27B is pressed, an operation is input. When an operation is input from the operation button 27A or 27B, the treatment instrument 1 is activated in the designated activation mode. In the same manner as the well-known treatment instruments, any one or more of a high-frequency current, ultrasonic vibration, and heat from a heater is supplied as treatment energy to the treatment target that is being held between the gripping pieces (jaws) 16 and 17. An example structure may be such that, when the treatment instrument 1 is activated in a specific activation mode based on the operation that is input from the operation button 27A or 27B, the electric motor is driven so as to staple the treatment target that is being held between the gripping pieces 16 and 17.

FIG. 3 shows the internal configuration of the housing 2. A cross-sectional view approximately perpendicular to (i.e., intersecting) the width direction of the housing 2 is presented in FIG. 3. The bend drive members 28A and 28B, and the configuration for transmitting the operation force from the bend dial 23 to the bend drive members 28A and 28B are omitted from FIG. 3. As shown in FIG. 3, a cylindrical movable member 31 is attached to the rotation member from the proximal side (arrow C2 side) inside the housing (housing main body 11). The movable member 31 extends along the reference rotation axis R (longitudinal axis C), and is movable along the reference rotation axis R with respect to the housing 3 and the shaft 3 (rotation member 25). The rotation of the movable member 31 around the reference rotation axis R is regulated with respect to the shaft 3, but the movable member 31 is rotatable together with the shaft 3 and the end effector 5 around the reference rotation axis R with respect to the housing 2.

A slide member 32 is arranged on the outer peripheral surface of the movable member 31 inside the housing 2. The handle 21 is coupled to the movable member 31 with the slide member 32 interposed in-between. The movable member 31 is rotatable around the reference rotation axis R with respect to the handle 21. Furthermore, the drive rod 33, which is an open/close drive member, is fixed to the movable member 31 through the coupling pin 35 inside the housing 2. The drive rod 33 extends from the inside of the movable member 31 through the inside of the shaft 3 along the reference rotation axis R. Because of the drive rod 33 that is fixed to the movable member 31, the drive rod 33 rotates together with the shaft 3, the end effector 5, and the movable member 31 around the reference rotation axis R with respect to the housing 2 when the operation force is applied by the rotation member 25.

Furthermore, when an operation force is applied to the handle 21, the handle 21 is opened or closed with respect to the grip 12. In this manner, the movable member 31 and the drive rod 33 are moved along the reference rotation axis R (longitudinal axis C) with respect to the shaft 3 and the housing 2. As shown in FIG. 2, one end (distal end) of the drive rod (drive member) 33 extending through the inside of the shaft 3 is coupled to the first gripping piece (first jaw) 16 of the end effector 5. In the present embodiment, the drive rod 33 is coupled to the first gripping piece 16 by a coupling pin 36. In accordance with the movement of the movable member 31 and the drive rod (drive member) 33 along the reference rotation axis R, at least the first gripping piece 16 pivots around the support pin (supporter) 19 with respect to the intermediary member 15. In this manner, the gripping pieces 16 and 17 open and close with respect to each other. Here, the support pin 19 serves as the fulcrum in pivoting of the first gripping piece 16, while the coupling pin 36 serves as the point of the drive force that is applied from the drive rod 33 to the first gripping piece 16. In an example structure in which the second gripping piece (second jaw) 17 is also rotatable with respect to the intermediary member 15, the distal end of the drive rod (open/close drive member) 33 is coupled not only to the first gripping piece 16, but also to the second gripping piece 17. If this is the case, both the gripping pieces 16 and 17 pivot with respect to the intermediary member 15 in accordance with the movement of the drive rod 33 along the reference rotation axis R, thereby opening and closing the gripping pieces 16 and 17 with respect to each other.

According to this embodiment, by opening the handle 21 with respect to the grip 12, the movable member 31 and the drive rod 33 are moved toward the distal side. On the other hand, by closing the handle with respect to the grip 12, the movable member 31 and the drive rod 33 are moved toward the proximal side. Moreover, according to this embodiment, the support pin 19 (the rotation axis T1 of the first gripping piece 16) is arranged on the opening side (arrow X1 side) of the first gripping piece 16 with respect to the coupling position (the coupling pin 36) of the drive rod 33 connected to the first gripping piece 16. With such an arrangement, when the drive rod (drive member) 33 moves to the distal side by opening the handle 21 with respect to the grip 12, the first gripping piece 16 opens with respect to the second gripping piece 17 so that the gripping pieces 16 and 17 are opened with respect to each other. On the other hand, when the drive rod (drive member) 33 is moved toward the proximal side by closing the handle 21 with respect to the grip 12, the first gripping piece 16 is closed with respect the second gripping piece 17 so that the gripping pieces 16 and 17 are closed with respect to each other.

A biasing member 37 such as a spring is provided inside the housing 2. The biasing member 37 has one end coupled to the housing 2 and the other end coupled to the handle 21. The biasing member 37 urges the handle 21 and brings the handle 21 into an open state with respect to the grip 12. The movable member 31 and the drive rod (drive member) 33 are therefore urged toward the distal side. The biasing member 37 urges the first gripping piece 16 into the open state with respect to the second gripping piece 17, and urges the end effector 5 into the state in which the gripping pieces 16 and 17 are opened with respect to each other.

The housing main body 11 of the housing 2 is provided with an engagement protrusion 41 that protrudes toward the inner peripheral side of the housing main body 11. The engagement protrusion 41 is provided in the entire periphery around the reference rotation axis R (the longitudinal axis C). Engagement protrusions 41 may be formed, for example, at predetermined intervals (not shown) around the reference rotation axis R (the longitudinal axis C). Thus, there may be one engagement protrusion 41 or a plurality of engagement protrusions 41. The rotation member 25, which is part of the shaft 3, is provided with an engagement recess 42 that is recessed toward the inner peripheral side. The engagement recess 42 is provided in the entire periphery around the reference rotation axis R. The engagement protrusion 41 engages with the engagement recess 42 so that the shaft 3 can be attached to the housing 2. The engagement recess 42 is movable around the reference rotation axis R with respect to the engagement protrusion 41. As a result, the shaft 3 (rotation member 25) is rotatable around the reference rotation axis R with respect to the housing 2. The engagement protrusion 41 and the engagement recess 42 therefore serve as a joint (coupling part) 40 that couples the shaft 3 with the housing 2 rotatable around the reference rotation axis R.

Figure 5:
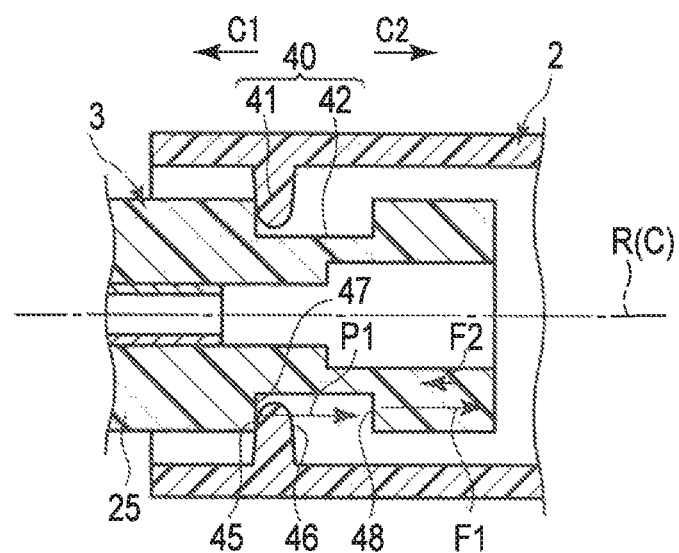
FIG. 5 is a cross-sectional view schematically showing the joint between the shaft and the housing, with the gripping pieces being in a closed state according to the first embodiment.

FIGS. 4 and 5 show the configuration of the joint 40 (engagement protrusion 41 and engagement recess 42) for the shaft 3 and housing FIG. 4 shows a state in which the gripping pieces 16 and 17 are open, and FIG. 5 shows a state in which the gripping pieces 16 and 17 are closed. As shown in FIGS. 4 and 5, the engagement protrusion 41 includes a protrusion opposing surface (first receiving surface) 45 facing the distal side, and a protrusion opposing surface (second receiving surface) 46 facing the proximal side. The engagement recess 42 includes a recess opposing surface (first contact surface) 47 facing the proximal side, and a recess opposing surface (second contact surface) 48 facing the distal side. The protrusion opposing surface 45 is opposed to the recess opposing surface 47, and the protrusion opposing surface 46 is opposed to the recess opposing surface 48.

The engagement recess 42 is movable (for a small movement) along the reference rotation axis R with respect to the engagement protrusion 41. The shaft 3 is therefore movable (for a small movement) along the reference rotation axis R (longitudinal axis C) with respect to the housing 2. The movement of the shaft 3, however, along the reference rotation axis R with respect to the housing 2 is performed in a very small range. When the recess opposing surface (first contact surface) 47 of the engagement recess 42 abuts on the protrusion opposing surface (first receiving surface) 45 of the engagement protrusion 41, the movement of the shaft 3 toward the proximal side with respect to the housing 2 is regulated. When the recess opposing surface (second contact surface) 48 of the engagement recess 42 abuts on the protrusion opposing surface (second receiving surface) 46 of the engagement protrusion 41, the movement of the shaft 3 toward the distal side with respect to the housing 2 is regulated.

When the handle 21, which serves as an opening closing operation input member, receives an operation force and is thereby closed with respect to the grip 12 against the bias from the biasing member 37, the movable member 31 and the drive rod 33 move toward the proximal side against the bias from the biasing member 37. For this reason, the first gripping piece 16 is closed with respect to the second gripping piece 17 against the bias from the biasing member 37, and the gripping pieces 16 and 17 are closed with respect to each other. When the gripping pieces 16 and 17 are closed against the bias, an axial force (first axial force) F1 acts on the shaft 3 toward the proximal side in a direction along the reference rotation axis R from the drive rod (drive member) 33 via the first gripping piece 16 and the support pin (support portion) 19 according to the present embodiment. That is, the axial force F1 acts on the shaft 3 toward the same side as the side to which the drive rod (open/close drive member) 33 moves by the closing operation of the handle 21. Furthermore, an axial force (second axial force) F2 acts on the shaft 3 under the bias from the biasing member 37, in a direction opposite to the axial force F1 via the drive rod 33, the first gripping piece 16 and the support pin 19. According to the present embodiment, the axial force F2 acts on the shaft 3 toward the distal side in the direction along the reference rotation axis R.

When no operation force is applied to the handle 21, keeping the gripping pieces 16 and 17 open under the bias from the biasing member 37, the axial force (first axial force) F1 related to the operation force of the handle 21 does not act on the shaft 3. This means that only the axial force (second axial force) F2 caused by the bias from the biasing member 37 acts on the shaft 3 toward the distal side, and thus the recess opposing surface (second contact surface) 48 of the rotation member 25 (shaft 3) abuts on the protrusion opposing surface (second reception surface) 46 of the housing 2 in the joint 40.

When the operation force is applied to the handle 21, thereby keeping the gripping pieces 16 and 17 closed against the bias of the biasing member 37, the axial force (first axial force) F1 that is greater than the axial force (second axial force) F2 acts on the shaft 3 in a direction opposite to the axial force F2. Thus, when, the gripping pieces 16 and 17 are closed against the bias, the shaft 3 moves (for a small movement) toward, the proximal, side, from the state of the recess opposing surface (second contact surface) 48 abutting on the protrusion opposing surface 46 of the housing 2, the proximal side being a side toward which the axial force F1 acts. That is, the shaft 3 moves to the same side as the side to which the drive rod (open/close drive member) 33 moves in accordance with the closing operation of the handle 21. As a result, with the gripping pieces 16 and 17 being closed, the recess opposing surface (first contact surface) 47 of the rotation member 25 (shaft 3) abuts on the protrusion opposing surface (first receiving surface) 45 of the housing 2 in the joint 40.

Here, in a state of the recess opposing surface (first contact surface) 47 of the shaft 3 abutting on the protrusion opposing surface 45 of the housing 2, the axial force (first axial force) F1 that is larger than the bias-related axial force (second axial force) F2 acts on the shaft 3. With this large axial force F1 acting on the shaft 3, a pressing force (first pressing force) P1 from the recess opposing surface (first contact surface) 47 to the protrusion opposing surface 45 becomes large when the recess opposing surface 47 abuts on the protrusion opposing surface 45. On the other hand, the bias from the biasing member 37 is smaller than the operation force and the like applied to the handle 21, and therefore the axial force (second axial force) F2 caused by the bias is small. For this reason, when the recess opposing surface (second contact surface) 48 of the shaft 3 abuts on the protrusion opposing surface 46 of the housing 2, the pressing force (second processing force) P2 from the recess opposing surface (second contact surface) 48 to the protrusion opposing surface 46 is small. According to the present embodiment, the pressing force (first pressing force) P1 applied from the recess opposing surface (first contact surface) 47 to the protrusion opposing surface 45 in the state of the recess opposing surface 47 abutting on the housing 2 is larger than the pressing force (second pressing force) P2 applied from the recess opposing surface (second contact surface) 48 to the protrusion opposing surface 46 in the state of the recess opposing surface 48 abutting on the housing 2.

Since the pressing force P1 is larger than the pressing force P2, the first rotation sliding resistance (first rotation sliding resistance) γ1 between the recess opposing surface (first contact surface) 47 and the housing 2 around the reference rotation axis R, in the state of the recess opposing surface 47 abutting on the protrusion opposing surface 45, is larger than the rotation sliding resistance (second rotation sliding resistance) γ2 between the recess opposing surface (second contact surface) 48 and the housing 2 around the reference rotation axis R, in the state of the recess opposing surface 48 abutting on the protrusion opposing surface 46. The rotation sliding resistances γ1 and γ2 denote the sliding resistances that suppress the rotation of the shaft 3 around the longitudinal axis C. Because the rotation sliding resistance (first rotation sliding resistance) γ1 is larger, this rotation sliding resistance γ1 regulates the movement of the engagement recess 42 around the reference rotation axis R with respect to the engagement protrusion 41 in the state in which the gripping pieces 16 and 17 are closed and the recess opposing surface 47 abuts on the protrusion opposing surface 45. As a result, the rotation of the shaft 3 and the end effector 5 around the reference rotation axis R with respect to the housing 2 is suppressed. That is, in the state of the recess opposing surface (first contact surface) 47 abutting on the protrusion opposing surface 45 of the housing 2, the rotation of the shaft 3 around the reference rotation axis R, which is caused by the force that acts on the end effector 5, can be suppressed.

In contrast, because the rotation sliding resistance γ2 is smaller, the rotation sliding resistance (second rotation sliding resistance) γ2 hardly regulates the movement of the engagement recess 42 around the reference rotation axis R with respect to the engagement protrusion 41 in the state in which the gripping pieces 16 and 17 are opened and the recess opposing surface 48 abuts on the protrusion opposing surface 46. This means that the rotation of the shaft 3 and the end effector 5 around the reference rotation axis R with respect to the housing 3 is also hardly suppressed. Thus, in the state of the recess opposing surface (second contact surface) 48 abutting on the protrusion opposing surface 46 of the housing 2, the shaft 3 and the end effector 5 are rotated together around the rotation axis R with respect to the housing 2 in accordance with the rotation of the rotation member 25.

Next, the function and effects of the treatment instrument 1 according to this embodiment will be described. When treating a living tissue or any treatment target using the treatment instrument 1, the surgeon holds the housing 2 in hand, and inserts the end effector 5 into a body cavity such as the abdominal cavity. Thereafter, the surgeon may rotate the rotation member 25 to rotate the shaft 3 and the end effector 5 around the reference rotation axis R, or may manipulate the bend dial 23 to bend the end effector 5 with respect to the shaft 3. In this manner, the position and orientation of the end effector 5 can be adjusted in the body cavity.

When the end effector 5 is bent, or when the end effector 5 and the shaft 3 are rotated around the reference rotation axis R, no operation force is applied to the handle 21. For this reason, the bias from the biasing member 37 maintains the gripping pieces 16 and 17 in the open state, and with the axial force (second axial force) F2 caused by the bias, the recess opposing surface (second contact surface) 48 comes to abut on the protrusion opposing surface (second receiving surface) 46 of the housing 2. As described above, since the axial force F2 is small, the rotation sliding resistance (second rotation sliding) γ2 between the recess opposing surface (second contact surface) 48 and the protrusion opposing surface 46 is small in the state of the recess opposing surface 48 abutting on the housing 2. For this reason, the rotation of the shaft 3 and the end effector 5 around the reference rotation axis R with respect to the housing 2 would hardly be suppressed by the rotation sliding resistance γ2. Thus, by rotating the rotation member 25, the shaft 3 and the end effector 5 are rotated together around the reference rotation axis R with respect to the housing 2, and the angular position of the end effector 5 around the reference rotation axis R thereby can be easily adjusted.

After the position and orientation of the end effector 5 is adjusted in a manner so that the treatment target is placed between the gripping pieces 16 and 17, the handle 21 is closed with respect to the grip 12 so that the gripping pieces 16 and 17 are closed against the bias of the biasing member 37. In this manner, the treatment target is held between the gripping pieces 16 and 17. When an operation is input from the operation button (27A or 27B) with the treatment target being held, the treatment instrument 1 is activated. In the designated activation mode so that, as described above, treatment energy (high-frequency current etc.) may be applied to the treatment target that is being held, or the treatment target may be stapled.

Here, in the treatment using the treatment instrument 1, force may be applied to the end effector 5 when the end effector 5 is bent with respect to the shaft 3 (reference rotation axis R) and the treatment target is being held between the gripping pieces 16 and 17 (i.e., in the closed state of the gripping pieces 16 and 17). If this happens, since the force acting on the end effector 5 is applied at a position away from the center axis (reference rotation axis R) of the shaft 3, there is a possible that a rotation moment may be generated around the reference rotation axis R (around the center axis of the shaft 3) by the force that acts on the end effector 5.

According to the present embodiment, in the state in which the operation force is applied to the handle 21 and the gripping pieces 16 and 17 are closed against the bias of the biasing member 37, the axial force (first axial force) F1 that is larger than the second axial force F2 acts on the shaft 3 in a direction opposite to the axial force F2. In the state of the gripping pieces 16 and 17 being closed, due to the axial force (first axial force) F1 produced by the operation force onto the handle 21, the recess opposing surface (first contact surface) 47 of the shaft 3 abuts on the protrusion opposing surface (first receiving surface) 45 of the housing 2. When the recess opposing surface 47 abuts on the housing 2 under this axial force F1, the rotation sliding resistance (first rotation sliding resistance) γ1 is generated between the recess opposing surface (first contact surface) 47 and the protrusion opposing surface 45. Thus, in the state in which the gripping pieces 16 and 17 are closed and the recess opposing surface (first contact surface) 47 abuts on the housing 2, the rotation sliding resistance γ1 around the reference rotation axis R suppresses the rotation of the shaft 3 and the end effector 5 around the reference rotation axis R with respect to the housing 2. Here, the rotation sliding resistance (first rotation sliding resistance) γ1 increases as the axial force F1 increases. The suppression effect (brake effect) for the rotation of the shaft 3 and the end effector 5 around the reference rotation axis R with respect to the housing 2 increases as the rotation sliding resistance γ1 increases. As a result, even if a rotation moment is generated around the reference rotation axis R by the force acting on the end effector 5, the rotation of the end effector 5 and the shaft 3 around the reference rotation axis R, which is caused by the force acting on the end effector 5, can be suppressed.

As described above, according to the present embodiment, even if a force acts on the end effector 5 in the closed state of the gripping pieces 16 and 17 and generates a rotation moment around the reference rotation axis R, the rotation sliding resistance γ1 between the recess opposing surface (first contact surface) 47 and the housing 2 effectively prevents the end effector 5 and the shaft 3 from being rotated around the reference rotation axis R. This reliably ensures the treatment performance in a treatment performed in the state in which the end effector 5 is being bent with respect to the shaft 3, and the treatment target is being held between the gripping pieces 18 and 17.

According to the present embodiment, the rotation sliding resistance γ1 is produced at the joint (coupling) 40 between the shaft 3 and the housing 2. Such an arrangement allows the rotation sliding resistance γ1 to be produced, without requiring extra components other than the housing 2, the shaft 3, the end effector 5, the handle 21, the movable member 31, and the drive rod (open/close drive member) 33, the movable member 31 and the drive rod (open/close drive member) 33 transmitting the operation force of the handle 21 to the end effector 5. Therefore, without complicating its configuration, it can be designed to suppress, only in the closed state of the gripping pieces 16 and 17, the rotation of the shaft 3 and the end effector 5 around the reference rotation axis R with respect to the housing 2.

(Modifications)

Figure 6:
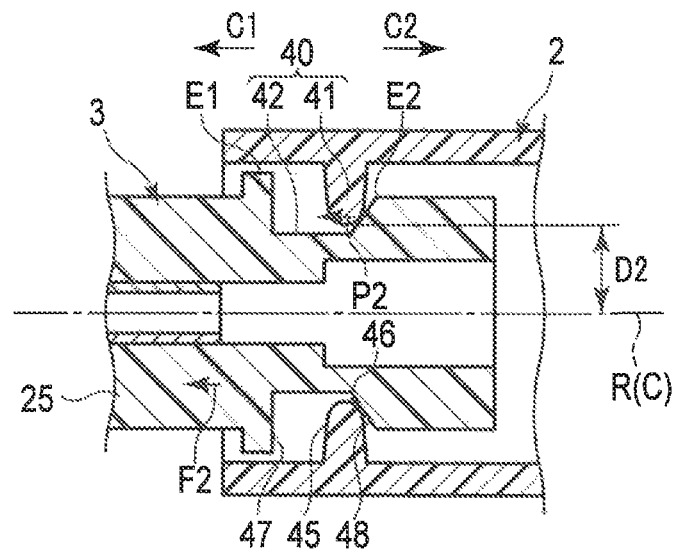
FIG. 6 is a cross-sectional view schematically showing the joint between the shaft and the housing, with the gripping pieces being in the open state according to a first modification.
Figure 7:
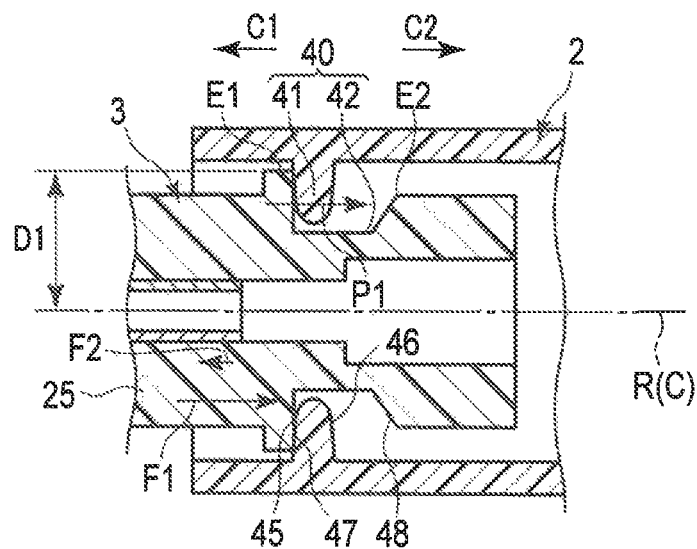
FIG. 7 is a cross-sectional view schematically showing the joint between the shaft and the housing, with the gripping pieces being in the closed state according to the first modification.

In the first modification shown in FIGS. 6 and 7, the recess opposing surface (first contact surface) 47 of the shaft 3 (rotation member 25) is formed to be approximately perpendicular to the reference rotation axis R. On the other hand, the recess opposing surface (second contact surface) 48 is slanted in a state in which the recess opposing surface 48 extends toward the proximal side (arrow C2 side) as extending toward the outer peripheral side. The outer peripheral end E1 of the recess opposing surface 47 is located on the outer peripheral side in comparison with the outer peripheral end E2 of the recess opposing surface 48.

With the above configuration, the recess opposing surface (first contact surface) 47 abuts on the protrusion opposing surface (first receiving surface) 45 at a portion away from the reference rotation axis R in the radial direction, in the closed state of the gripping pieces (jaws) 16 and 17. This means that the distance (first distance) D1 from the reference rotation axis R to the abutting portion between the outer peripheral end E1 of the recess opposing surface 47 and the protrusion opposing surface 45, is larger than the distance (second distance) D2 from the reference rotation axis R to the abutting portion of the outer peripheral end E2 of the recess opposing surface 48 and the protrusion opposing surface 46. As the portion of the recess opposing surface (first contact surface) 47 abutting on the housing 2 is further away from the reference rotation axis R, the moment of the frictional force around the reference rotation axis R between the recess opposing surface (first contact surface) 47 and the protrusion opposing surface (first receiving surface) 45 becomes larger. Thus, as the distance D1 increases, the rotation sliding resistance (first rotation sliding resistance) γ1 between the recess opposing surface (first contact surface) 47 and the housing 2 around the reference rotation axis R increases in the state of the recess opposing surface 47 abutting on the protrusion opposing surface 45. Furthermore, with the above-described configuration, as the distance D1 increases, the contact area (first contact area) S1 between the recess opposing surface 47 and the protrusion opposing surface 45 increases in the closed state of the gripping pieces 16 and 17. With the frictional force between the recess opposing surface (first contact surface) 47 and the protrusion opposing surface (first receiving surface) 45 increased by adjusting the distance D1, the rotation sliding resistance (first rotation sliding resistance) γ1 between the recess opposing surface (first contact surface) 47 and the housing 2 around the reference rotation axis R increases. As the rotation sliding resistance γ1 increases, the rotation of the shaft 3 and the end effector 5 around the reference rotation axis R with respect to the housing 2 is suppressed in the closed state of the gripping pieces 16 and 17.

Furthermore, with the above configuration, in the open state of the gripping pieces 16 and 17, the recess opposing surface (second contact surface) 48 abuts on the protrusion opposing surface (second reception surface) 46 at a portion closer to the reference rotation axis R in the radial direction. The distance (second distance) D2 from the reference rotation axis R to the abutting portion between the recess opposing surface 48 and the protrusion opposing surface 46 therefore becomes smaller than the above-mentioned distance (first distance) D1. With the recess opposing surface (second contact surface) 48 abutting on the housing 2 at a portion close to the reference rotation axis R, the moment of the frictional force between the recess opposing surface (second contact surface) 48 and the protrusion opposing surface (second receiving surface) 46 around the reference rotation axis R is reduced. Thus, as the distance D2 decreases, the rotation sliding resistance (second rotation sliding resistance) γ2 between the recess opposing surface (second contact surface) 48 and the housing 2 around the reference rotation axis R is reduced in the state of the recess opposing surface 48 abutting on the protrusion opposing surface 46. Furthermore, with the above-described configuration, the contact area (second contact area) S2 between the recess opposing surface 48 and the protrusion opposing surface 46 is reduced, as the distance D2 becomes shorter in the open state of the gripping pieces 16 and 17. Here, with the distance D2 being shorter than the distance D1, the contact area (second contact area) S2 is smaller than the aforementioned contact area (first contact area) S1. By adjusting the distance D2 to reduce the frictional force between the recess opposing surface (second contact surface) 48 and the protrusion opposing surface (second receiving surface) 46, the rotation sliding resistance (second rotation sliding resistance) γ2 between the recess opposing surface (second contact surface) 48 and the housing 2 around the reference rotation axis R can be reduced. With the reduced rotation sliding resistance γ2, even when the operation force applied to the rotation member 25 is small in the open state of the gripping pieces 16 and 17, the shaft 3 and the end effector 5 can be smoothly rotated around the reference rotation axis R with respect to the housing 2.

In the second modification as illustrated in FIG. 8, a pad 51 formed of a material having a high friction coefficient, such as rubber, is provided in the engagement recess 42 of the shaft 3 (rotation member 25). The recess opposing surface (first contact surface) 47 is formed by this pad 51. The recess opposing surface (first contact surface) 47 therefore has a friction coefficient that is higher than the recess opposing surface (second contact surface) 48, which is not formed by the pad 51.

By adopting the configuration as described above, the frictional force between the recess opposing surface (first contact surface) 47 and the protrusion opposing surface (first receiving surface) 45 increases in the closed state of the gripping pieces 16 and 17, which further increases the rotation sliding resistance (first rotation sliding resistance) γ1 between the recess opposing surface (first contact surface) 47 and the housing 2 around the reference rotation axis R. With the increased rotation sliding resistance γ1, the rotation of the shaft 3 and the end effector 5 around the reference rotation axis R with respect to the housing 2 is further suppressed in the closed state of the gripping pieces 16 and 17.

In the third modification as illustrated in FIG. 9, an uneven serrated surface 52 is provided on the recess opposing surface (first contact surface) 47 of the shaft 3 so that the serrated surface 52 of the recess opposing surface 47 abuts on the protrusion opposing surface (first receiving surface) 45 in the closed state of the gripping pieces 16 and 17. In comparison with the recess opposing surface (second contact surface) 48, a large frictional force is generated on the serrated surface 52. In a manner similar to the second modification, the frictional force between the recess opposing surface (first contact surface) 47 and the protrusion opposing surface (first receiving surface) 45 is increased in the closed state of the gripping pieces 16 and 17 in the present modification, and therefore the rotation sliding resistance (first rotation sliding resistance) γ1 between the recess opposing surface (first contact surface) 47 and the housing 2 around the reference rotation axis R is further increased.

In the fourth modification as illustrated in FIG. 10, a protuberance 53 is formed on the recess opposing surface (first contact surface) 47 of the shaft 3 to protrude toward the protrusion opposing surface (first receiving surface) 45, and a hollow 55 is formed in the protrusion opposing surface 45 of the housing 2 in a manner that the protuberance 53 can be engaged therewith. The protuberance 53 is engaged with the hollow 55 when the gripping pieces 16 and 17 are closed with respect to each other, and the recess opposing surface (first contact surface) 47 abuts on the protrusion opposing surface (first receiving surface) 45. With the engagement of the protuberance 53 with the hollow 55, the frictional force between the recess opposing surface (first contact surface) 47 and the protrusion opposing surface (first receiving surface) 45 increases, and the rotation sliding resistance (first rotation sliding resistance) γ1 around the reference rotation axis R is further increased between the recess opposing surface (first contact surface) 47 and the housing 2.

In the fifth modification as illustrated in FIG. 11, a protuberance 57 is formed in the protrusion opposing surface (first receiving surface) 45 of the housing 2 to protrude toward the recess opposing surface (first contact surface) 47, and a hollow 58 is formed in the recess opposing surface 47 of the shaft 3 in a manner so that the protuberance 57 can be engaged therewith. In this modification, the same function and effect as the fourth modification are exhibited.

In the sixth modification as illustrated in FIG. 12, a protuberance 59 is formed on the recess opposing surface (first contact surface) 47 of the shaft 3 to protrude toward the protrusion opposing surface (first receiving surface) 45. In the closed state of the gripping pieces 16 and 17, the projecting end of the protuberance 59 of the recess opposing surface (first contact surface) 47 abuts on the protrusion opposing surface (first receiving surface) 45. The recess opposing surface 47 abuts on the protrusion opposing surface 45 at the projecting end of the protuberance 59 so that the frictional force between the recess opposing surface (first contact surface) 47 and the protrusion opposing surface (first receiving surface) 45 increases. The rotation sliding resistance (first rotation sliding resistance) γ1 around the reference rotation axis R is thereby further increased between the recess opposing surface (first contact surface) 47 and the housing 2. In a modification that is not shown, a protruding portion may be formed on the protrusion opposing surface (first receiving surface) 45 of the housing 2 to protrude toward the recess opposing surface (first contact surface) 47. In this modification, the same function and effect as the fifth modification are exhibited.

Figure 14:
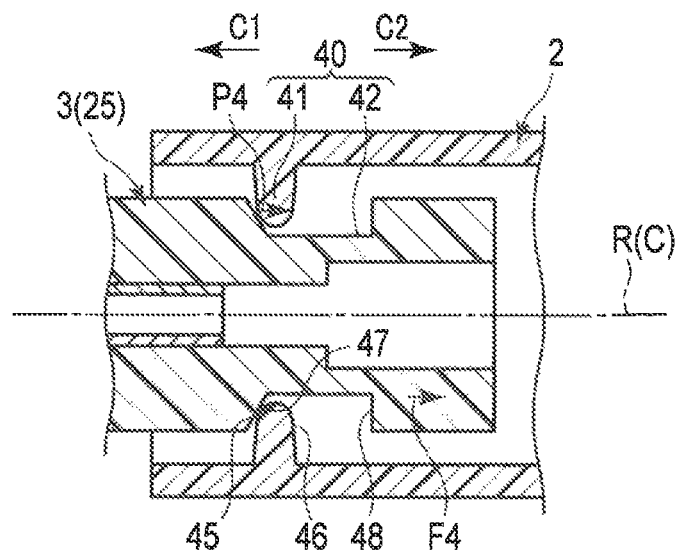
FIG. 14 is a cross-sectional view schematically showing the joint between the shaft and the housing, with the gripping pieces being in the open state according to the seventh modifidation.
Figure 15:
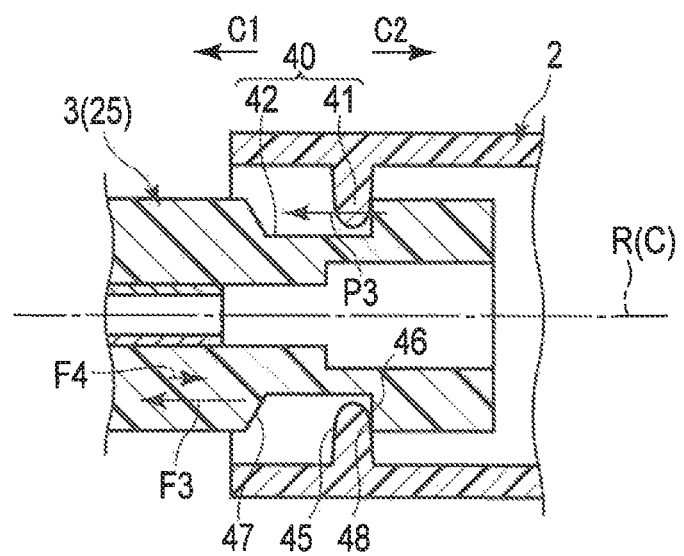
FIG. 15 is a cross-sectional view schematically showing the joint between the shaft and the housing, with the gripping pieces being in the closed state according to the seventh modification.

In the seventh modification as illustrated in FIGS. 13 to 15, the support pin 19 (the rotation axis T1 of the first gripping piece 16) is positioned on the closing side (arrow X2 side) of the first gripping piece 16 with respect to the coupling position (coupling pin 36) of the drive rod 33 coupled to the first gripping piece 16. Thus, in this modification, when the handle 21 is opened with respect to the grip 12, the drive rod (drive member) 33 is moved toward the proximal side. As the result, the first gripping piece (first jaw) 16 opens with respect to the second gripping piece (second jaw) 17, and the gripping pieces 16 and 17 are opened with respect to each other. On the other hand, when the handle 21 is closed with respect to the grip 12, the drive rod (drive member) 33 is moved toward the distal side. As the result, the first gripping piece 16 is closed with respect to the second gripping piece 17, the gripping pieces 16 and 17 are closed with respect to each other.

In this modification, when the operation force is applied to the handle 21, which serves as an opening/closing operation input member, thereby moving the movable member 31 and the drive rod 33 toward the distal side against the bias from the biasing member 37, the gripping pieces 16 and 17 are closed with respect to each other against the bias from the biasing member 37. With the gripping pieces 16 and 17 closed against the bias, an axial force (first axial force) F3 acts on the shaft 3 from the drive rod (drive member) 33 by way of the first gripping piece 16 and the support pin (support portion) 19 in a direction along the reference rotation axis R. An axial force (second axial force) F4 also acts on the shaft 3 in a direction opposite to the axial force F3 by way of the drive rod 33, the first gripping piece 16 and the support pin 19 under the bias from the biasing member 37. In this modification, the axial force F4 acts on the shaft 3 toward the proximal side in the direction along the reference rotation axis R.

In this modification, in the state of the operation force not applied to the handle 21 and the gripping pieces 16 and 17 opened under the bias of the biasing member 37, the axial force (first axial force) F3 caused by the operation force of the handle 21 does not act on the shaft 3. For this reason, only the axial force (second axial force) F4 produced by the bias from the biasing member 37 acts on the shaft 3 toward the proximal side, and the recess opposing surface (second contact surface) 47 of the rotation member 25 (shaft 3) abuts on the protrusion opposing surface (second receiving surface) 45 of the housing 2 in the joint 40.

In the state in which the operation force is applied to the handle 21 and the gripping pieces 16 and 17 are closed against the bias of the biasing member 37, the axial force (first axial force) F3 that is greater than the axial force (second axial force) F4 acts on the shaft 3 in a direction opposite to the axial force F4. Because the gripping pieces 16 and 17 are closed against the bias, the shaft 3 is moved (for a small movement) toward the distal side with respect to the housing 2 from the state in which the recess opposing surface (second contact surface) 47 abuts on the protrusion opposing surface 45 of the housing 2, the distal side being the side toward which the axial force F3 acts. Thus, the recess opposing surface (first contact surface) 48 of the rotation member 25 (shaft 3) abuts on the protrusion opposing surface (housing surface) 46 of the housing 2 in the joint 40.

Here, in the state of the recess opposing surface (first contact surface) 48 of the shaft 3 abutting on the protrusion opposing surface 46 of the housing 2, the axial force (first axial force) F3 that is larger than the axial force (second axial force) F4 produced by the bias acts on the shaft 3. For this reason, in this modification, the pressing force (first pressing force) P3 from the recess opposing surface (first contact surface) 48 to the protrusion opposing surface 46, in the state of the recess opposing surface 48 abutting on the housing 2, is greater than the pressing force (second pressing force) P4 from the recess opposing surface (second contact surface) 47 to the protrusion opposing surface 45, in the state of the recess opposing surface 47 abutting on the housing 2. With the axial force F3, the rotation sliding resistance (first rotation sliding resistance) γ3 is produced between the recess opposing surface (first contact surface) 48 and the protrusion opposing surface 46, in the state of the recess opposing surface 48 abutting on the housing 2. With the axial force F4, the rotation sliding resistance (second rotation sliding resistance) γ4 around the reference rotation axis R is produced between the recess opposing surface (second contact surface) 47 and the housing 2 in the state of the recess opposing surface 47 abutting on the protrusion opposing surface 45. With the pressing force P3 being greater than the pressing force P4, the first rotation sliding resistance (first rotation sliding resistance) γ3 between the recess opposing surface (first contact surface) 46 and the housing 2 around the reference rotation axis R, in the state of the recess opposing surface 48 abutting on the protrusion opposing surface 46, is greater than the rotation sliding resistance (second rotation sliding resistance) γ4 between the recess opposing surface (second contact surface) 47 and the housing 2 around the reference rotation axis R, in the state of the recess opposing surface 47 abutting on the protrusion opposing surface 45.

With the rotation sliding resistance γ3 being large in the present modification, the rotation sliding resistance (first rotation sliding resistance) γ3 regulates the movement of the engagement recess 42 around the reference rotation axis R with respect to the engagement protrusion 41 in the state of the gripping pieces 16 and 17 being closed and the recess opposing surface 48 abutting on the protrusion opposing surface 46. Accordingly, the rotation of the shaft 3 and the end effector 5 around the reference rotation axis R with respect to the housing 2 can be suppressed. In the present modification, the rotation of the shaft 3 around the reference rotation axis R caused by the force acting on the end effector 5 is suppressed in the closed state of the gripping pieces 16 and 17.

On the other hand, with the rotation sliding resistance γ4 being small, the movement of the engagement recess 42 around the reference rotation axis R with respect to the engagement protrusion 41 is hardly regulated by the rotation sliding resistance (second rotation sliding resistance) γ4 in the state of the gripping pieces 16 and 17 being opened and the recess opposing surface 47 abutting on the protrusion opposing surface 45. This means that the rotation of the shaft 3 and the end effector 5 around the reference rotation axis R with respect to the housing 2 would also be hardly suppressed. In this modification, by rotating the rotation member 25 in the open state of the gripping pieces 16 and 17, the shaft 3 and the end effector 5 are also rotated together around the reference rotation axis R with respect to the housing 2. With the configuration as described above, the present modification exhibits the same function and effects as in the first embodiment.

As the seventh modification, in the configuration in which the gripping pieces 16 and 17 are closed with the drive rod (open/close drive member) 33 moving toward the distal side, the rotation sliding resistance γ3 between the recess opposing surface (first contact surface) 48 and the housing 2 may be increased in the same manner as in any of the configurations of the first to sixth modifications, in which the rotation sliding resistance γ1 is increased. As in the seventh modification, in the configuration in which the gripping pieces 16 and 17 are closed with the drive rod (open/close drive member) 33 moving toward the distal side, the rotation sliding resistance γ4 between the recess opposing surface (second contact surface) 47 and the housing 2 may be reduced in a manner similar to the configurations of the first modification, in which the rotation sliding resistance γ2 is reduced.

Figure 16:
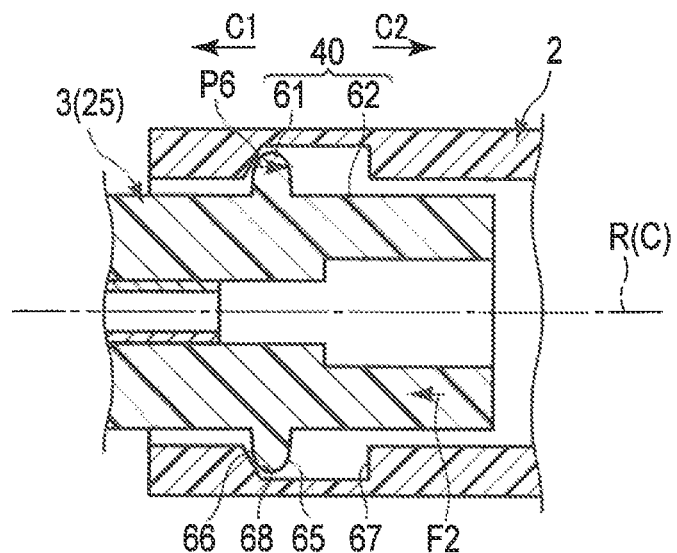
FIG. 16 is a sectional view schematically showing the joint between the shaft and the housing, with the gripping pieces being in the open state according to an eighth modification.
Figure 17:
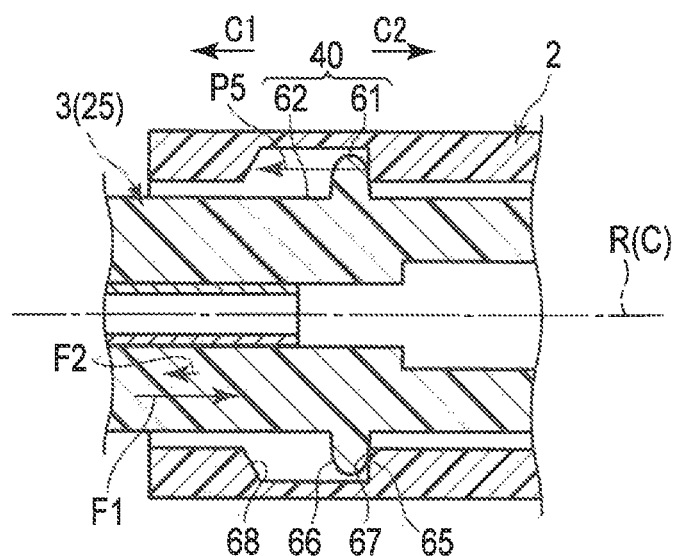
FIG. 17 is a sectional view schematically showing the joint between the shaft and the housing, with the gripping pieces being in the closed state according to the eighth modification.

In the eighth modification as illustrated in FIGS. 16 and 17, an engagement protrusion 61 protruding toward the outer peripheral side is provided on the shaft 3 including the rotation member 25, and an engagement recess 62 recessed toward the outer peripheral side is provided on the housing 2. In this modification, the engagement protrusion 61 comes to be engaged with the engagement recess 62 so that the shaft 3 is attached to the housing 2. Then, the engagement protrusion 61 and the engagement recess 62 form a joint (coupling part) 40, which connects the shaft 3 to the housing 2 rotably around the reference rotation axis R. The engagement protrusion 61 includes a protrusion opposing surface (first contact surface) 65 facing the proximal side, and a protrusion opposing surface (second contact surface) 66 facing the distal side. The engagement recess 62 includes a recess opposing surface (first receiving surface) 67 facing the distal side, and a recess opposing surface (second receiving surface) 68 facing the proximal side. The protrusion opposing surface 65 is opposed to the recess opposing surface 67, and the protrusion opposing surface 66 is opposed to the recess opposing surface 68.

In this modification, the engagement protrusion 61 is movable (for a small movement) along the reference rotation axis R with respect to the engagement recess 62, and the shaft 3 is movable (for a small movement) along the reference rotational axis R (longitudinal axis C) with respect to the housing 2. However, the movement of the shaft 3 along the reference rotation axis R with respect to the housing 2 is performed in a very small range. The protrusion opposing surface (first contact surface) 65 of the engagement protrusion abuts on the recess opposing surface (first receiving surface) 67 of the engagement recess 62, which regulates the movement of the shaft 3 toward the proximal side with respect to the housing 2. Then, with the protrusion opposing surface (second contact surface) 66 of the engagement protrusion 61 abutting on the recess opposing surface (second receiving surface) 68 of the engagement recess 62, the movement of the shaft 3 toward the distal side with respect to the housing 2 is regulated.

In this modification, as in the first embodiment, with the operation force applied to the handle 21, which serves as the opening/closing operation input member, and the gripping pieces 16 and 17 thereby being closed against the bias from the biasing member 37, the axial force (first axial force) F1 acts on the shaft 3 toward the proximal side in the direction along the reference rotation axis R from the drive rod (drive member) 33 via the first gripping piece 16 and the support pin (support portion) 19. In addition, the axial force (second axial force) F2 acts on the shaft 3 in a direction opposite to the axial force F1 (to the proximal side) via the drive rod 33, the first gripping piece 16, and the support pin 19 under the bias from the biasing member 37.

In this modification, the operation force (first axial force) F1 will not act on the shaft 3 when no operation force is applied to the handle 21 and the gripping pieces 16 and 17 are opened under the bias of the biasing member 37. As a result, only the axial force (second axial force) F2 produced by the bias from the biasing member 37 acts on the shaft 3 toward the proximal side, and the protrusion opposing surface (second contact surface) 66 of the rotation member 25 (shaft 3) abuts on the recess opposing surface (second receiving surface) 68 of the housing 2 in the joint 40.

When the operation force is applied to the handle 21 and the gripping pieces 16 and 17 are closed against the bias of the biasing member 37, the axial force (first axial force) F1 that is greater than the axial force (second axial force) F2 acts on the shaft 3 in a direction opposite to the axial force F2. With the gripping pieces 16 and 17 closed against the bias, the shaft 3 moves (for a small movement) toward the proximal side with respect to the housing 2 from the state of the protrusion opposing surface (second contact surface) 66 abutting on the recess opposing surface 68 of the housing 2, the proximal side being a side toward which the axial force F1 acts. As a result, in the joint 40, the protrusion opposing surface (rotation contact surface) 65 of the rotation member 25 (shaft 3) abuts on the recess opposing surface (first receiving surface) 67 of the housing 2.

Here, when the protrusion opposing surface (first contact surface) 65 of the shaft 3 abuts on the recess opposing surface 67 of the housing 2, the axial force (first axial force) F1 that is larger than the axial force (second axial force) F2 acts on the shaft 3. Thus, in this modification, the pressing force (first pressing force) P5 applied from the protrusion opposing surface (first contact surface) 65 to the recess opposing surface 67, in the state of the protrusion opposing surface 65 abutting on the housing 2, is larger than the pressing force (second pressing force) P6 applied from the protrusion opposing surface (second contact surface) 66 to the recess opposing surface 68, in the state of the protrusion opposing surface 66 abutting on the housing 2. Since the pressing force P5 is larger than the pressing force P6, the first rotation sliding resistance (first rotation sliding resistance) γ5 between the protrusion opposing surface (first contact surface) 65 and the housing 2 around the reference rotation axis R in the state of the protrusion opposing surface 65 abutting on the recess opposing surface 67 is greater than the rotation sliding resistance (second rotation sliding resistance) γ6 around the reference rotation axis R between the protrusion opposing surface (second contact surface) 66 and the housing 2 in the state of the protrusion opposing surface 66 abutting on the recess opposing surface 68.

In this modification, with the rotation sliding resistance γ5 being large, the rotation of the shaft 3 and the end effector 5 around the reference rotation axis R with respect to the housing 2 is suppressed by the rotation sliding resistance (first rotation sliding resistance) γ5 in the state of the gripping pieces 16 and 17 being closed and the protrusion opposing surface 65 abutting on the recess opposing surface 67. Therefore, in this modification, the rotation of the shaft 3 around the reference rotation axis R caused by the force acting on the end effector 5 can be suppressed, in the closed state of the gripping pieces 16 and 17.

On the other hand, with the rotation sliding resistance γ6 being small, the rotation of the shaft 3 and the end effector 5 around the reference rotation axis R with respect to the housing 2 would be hardly suppressed by the rotation sliding resistance (second rotation sliding resistance) γ6, in the state of the gripping pieces 16 and 17 being opened and the protrusion opposing surface 66 abutting on the recess opposing surface 68. In this modification, by rotating the rotation member 25 in the open state of the gripping pieces 16 and 17, the shaft 3 and the end effector 5 are rotated together around the reference rotation axis R with respect to the housing 2. With the configuration as described above, the present modification exhibits the same function and effects as in the first embodiment.

In the configuration in which the engagement protrusion 61 and the engagement recess 62 forms the joint 40 as in the eighth modification, the rotation sliding resistance $\gamma 5$ between the protrusion opposing surface (first contact surface) 65 and the housing 2 may be increased, in the same manner as in any of the configurations of the first to sixth modifications for increasing the rotation sliding resistance $\gamma 1$. Furthermore, in the configuration in which the engagement protrusion 61 and the engagement recess 62 forms the joint 40 as in the eighth modification, the rotation sliding resistance $\gamma 6$ between the protrusion opposing surface (second contact surface) 66 and the housing 2 may be reduced in the same manner as the configuration of the first modification in which the rotation sliding resistance $\gamma 2$ is reduced.

In a modification that is not shown, in the configuration in which the engagement protrusion 61 and the engagement recess 62 form the joint 40 as in the eighth modification, the gripping pieces 16 and 17 are closed by moving the drive rod (open/close drive member) 33 toward the distal side as in the seventh modification. In this modification, in the closed state of the gripping pieces 16 and 17, the protrusion opposing surface (first contact surface) 66 abuts on the recess opposing surface (first receiving surface) 68 under the axial force (first axial force) F3 that acts on the shaft 3 toward the distal side. Here, the pressing force (first pressing force) P7 acts from the protrusion opposing surface (first contact surface) 66 to the recess opposing surface 68, and the rotation sliding resistance (first rotation sliding resistance) $\gamma 7$ is thereby produced between the protrusion opposing surface 66 and the housing 2 around the reference rotation axis R. Furthermore, in this modification, in the open state of the gripping pieces 16 and 17, the protrusion opposing surface (second contact surface) 65 abuts on the recess opposing surface (second receiving surface) 67 of the housing 2 under the axial force (second axial force) F4 produced by the bias of the biasing member 37. Here, the pressing force (second pressing force) P8 acts from the protrusion opposing surface (second contact surface) 65 to the recess opposing surface 67, and the rotation sliding resistance (second rotation sliding resistance) $\gamma 8$ is thereby produced between the protrusion opposing surface 65 and the housing 2 around the reference rotation axis R. Here, in this modification, the pressing force P7 is larger than the pressing force P8, and the rotation sliding resistance $\gamma 7$ is larger than the rotation sliding resistance $\gamma 8$.

In the present modification, with the rotation sliding resistance $\gamma 7$ being large, the rotation of the shaft 3 and the end effector 5 around the reference rotation axis R with respect to the housing 2 is suppressed by the rotation sliding resistance (first rotation sliding resistance) $\gamma 7$, in the state of the gripping pieces 16 and 17 being closed and the protrusion opposing surface 66 abutting on the recess opposing surface 68. On the other hand, with the rotation sliding resistance $\gamma 8$ being small, the rotation of the shaft 3 and the end effector 5 around the reference rotation axis R with respect to the housing 2 is hardly suppressed by the rotation sliding resistance (second rotation sliding resistance) $\gamma 8$, in the state in which the gripping pieces 16 and 17 being opened and the protrusion opposing surface 65 abutting on the recess opposing surface 67.

In the configuration in which the rotation sliding resistance $\gamma 7$ is produced, the rotation sliding resistance $\gamma 7$ between the protrusion opposing surface (first contact surface) 66 and the housing 2 may be increased, in the same manner as in any of the configurations of the first to sixth modifications in which the rotation sliding resistance $\gamma 1$ is increased. Furthermore, in the configuration in which the rotation sliding resistance $\gamma 8$ is produced, the rotation sliding resistance $\gamma 8$ between the protrusion opposing surface (second contact surface) 65 and the housing 2 may be reduced in the same manner as in the configuration of the first modification in which the rotation sliding resistance $\gamma 2$ is reduced.

In the ninth modification as illustrated in FIGS. 18 and 19, a protrusion (shaft-side protrusion) 71 protruding toward the outer peripheral side is provided in a portion of the shaft 3 different from the joint 40 (engagement recess 42). A protrusion (housing-side protrusion) 72 protruding toward the inner peripheral side is provided in a portion of the housing 2 different from the joint 40 (engagement protrusion 41). In this modification, the protrusions 71 and 72 are located on the distal side with respect to the joint 40. The protrusion 71 includes a contact surface (first contact surface) 73 facing the proximal side. The protrusion 72 includes a reception surface (first receiving surface) 75 facing the distal side, and the reception surface 75 is opposed to the contact surface 73.

In the open state of the gripping pieces 16 and 17, only the axial force (second axial force) F2 produced by the bias of the biasing member 37 acts on the shaft 3 toward the distal side. Thus, the contact surface 73 is provided at a position away from the reception surface 75 to the distal side. As in the first embodiment, the recess opposing surface (second contact surface) 48 of the engagement recess 42 abuts on the protrusion opposing surface (second receiving surface) 46 of the engagement protrusion 41. Therefore, the rotation sliding resistance (second rotation sliding resistance) $\gamma 2$ is produced between the recess opposing surface (second contact surface) 48 and the housing 2 around the reference rotation axis R in the open state of the gripping pieces 16 and 17, similarly to the first embodiment.

In this modification, when the operation force is applied to the handle 21 and the gripping pieces 16 and 17 are closed against the bias of the biasing member 37, the axial force (first axial force) F1 that is greater than the axial force (second axial force) F2 acts on the shaft 3 in the direction opposite to the axial force F2. Under the axial force F1, the shaft 3 moves (for a small movement) toward the proximal side with respect to the housing 2 from the state of the recess opposing surface (second contact surface) 48 abutting on the protrusion opposing surface 46 of the housing. As a result, in the closed state of the gripping pieces 16 and 17, the contact surface 73 of the protrusion 71 abuts on the reception surface 75 of the protrusion 72.

When the contact surface (first contact surface) 73 abuts on the receiving surface (first receiving surface) 75, a pressing force (first pressing force) P9 acts from the contact surface 73 of the shaft 3 onto the reception surface 75 of the housing 2, and a rotation sliding resistance (first rotation sliding resistance) $\gamma 9$ is produced between the contact surface 73 of the shaft 3 and the housing 2 around the reference rotation axis R. Here, with the axial force F1 being large, the pressing force (first pressing force) P9 is larger than the aforementioned pressing force (second pressing force) P2, and the rotation sliding resistance (first rotation sliding resistance) $\gamma 9$ is larger than the aforementioned rotation sliding resistance (second rotation sliding resistance) $\gamma 2$.

With the rotation sliding resistance $\gamma 9$ being large, the movement of the protrusion 71 around the reference rotation axis R with respect to the protrusion 72 is regulated by the rotation sliding resistance (first rotation sliding resistance) γ9 in the state of the gripping pieces 16 and 17 being closed and the contact surface 73 abutting on the reception surface 75. Accordingly, the rotation of the shaft 3 and the end effector 5 around the reference rotation axis R with respect to the housing 2 is suppressed. In this manner, the rotation of the shaft 3 around the reference rotation axis R under the force acting on the end effector 5 is suppressed, in the state of the contact surface (first contact surface) 73 abutting on the reception surface 75 of the housing 2. In this modification, the same function and effects as in the first embodiment are exhibited.

Modifications may be made to the configuration in which the contact surface 73 of the shaft 3 is provided in a portion different from the joint 40 as in the ninth modification, in the same manner as any of the first to eighth modifications.

Figure 20:
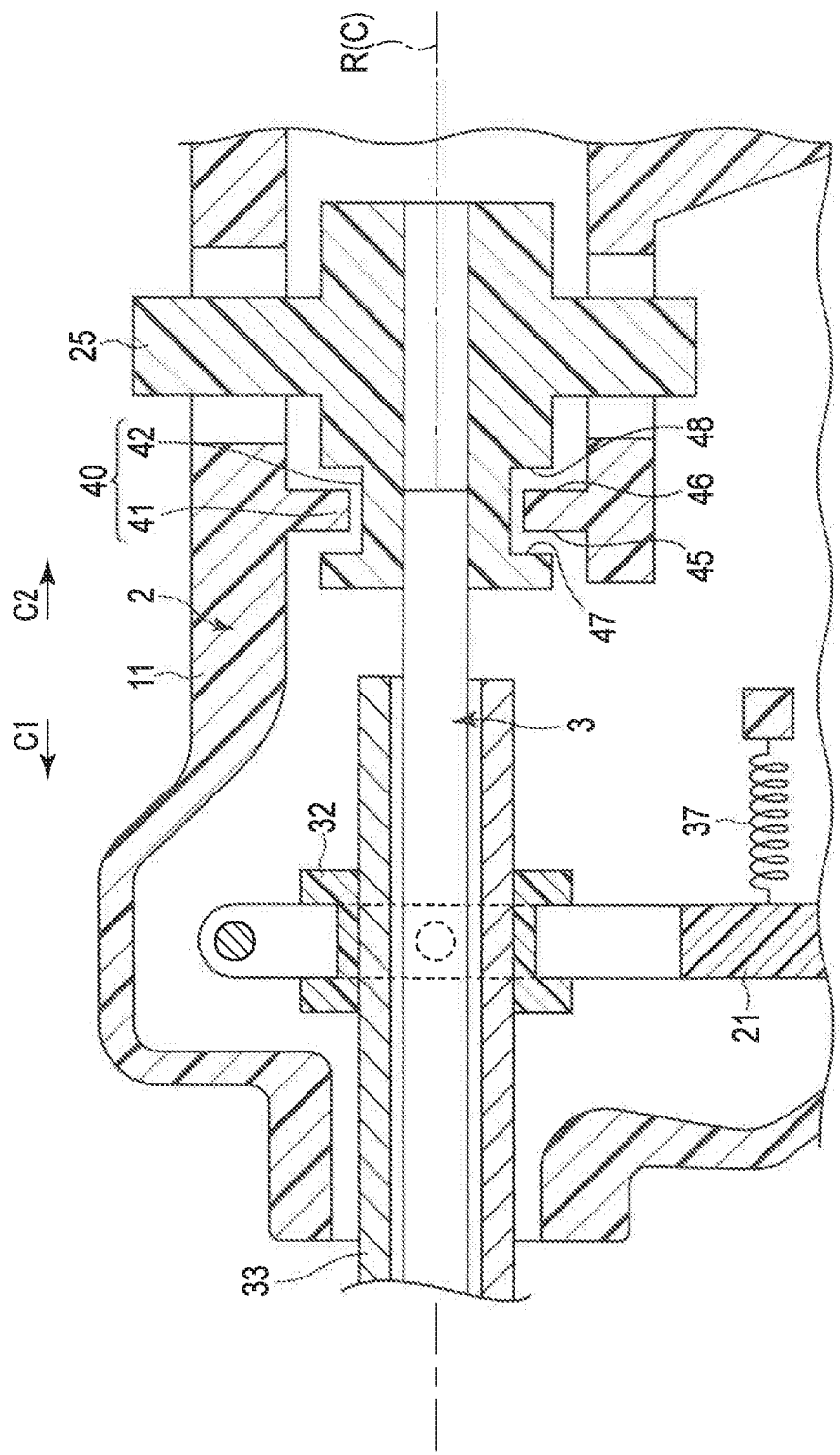
FIG. 20 is a cross-sectional view schematically showing the internal configuration of the housing according to a tenth modification.

In the above-mentioned embodiment, the drive rod 33, which serves as an open/close drive member, extends through the inside of the shaft 3. In the tenth modification shown in FIG. 20, the drive rod 33 that is the open/close drive member is formed in a cylindrical shape. The shaft 3 extends through the inside of the drive rod 33 along the reference rotation axis R. In this modification, the movable member 31 and the coupling pin 35 are not provided, and the handle 21 is attached to the drive rod 33 via the slide member 32 inside the housing 2. Furthermore, in this modification, the shaft 3 extends up to a part located on the proximal side with respect to the proximal end of the drive rod 33 inside the housing 2. The shaft 3 is provided with a rotating member (rotating knob) 25, the rotating member 25 being located on the proximal side with respect to the coupling position of the handle 21 coupled to the drive rod 33 and the proximal end of the drive rod 33. The rotation member 25 is provided with the engagement recess 42 that forms the joint 40. Therefore, in this modification, the engagement recess 42 is located on the proximal side with respect to the proximal end of the drive rod 33. In this modification, the housing 2 is provided with the engagement protrusion 41 to be engaged with the engagement recess 42, and the engagement protrusion 41 and the engagement recess 42 form the joint (coupling) 40 that couples the shaft 3 to the housing 2 in a rotatable manner around the reference rotation axis R. In this modification, the rotation member 25 is exposed to the outside on the outer surface of the housing main body 11, for example, in a portion facing in the width direction of the housing 2 and in a portion facing in a direction opposite to a side on which the grip 12 (handle 21) is arranged with respect to the reference rotation axis R.

Similarly to the first embodiment, the operation force is applied to the handle 21, which is the opening/closing operation input member, and the drive rod 33 is thereby moved toward the proximal side against the bias from the biasing member 37 in this modification. In this manner, the gripping pieces 16 and 17 are closed against the bias from the biasing member 37. Furthermore, with the gripping pieces 16 and 17 closed against the bias, the axial force (first axial force) F1 acts on the shaft 3 toward the proximal side in a direction along the rotation axis R via the first gripping piece 16 and the support pin (supporter) 19 from the drive rod (drive member) 33. In addition, under the bias of the biasing member 37, the axial force (second axial force) F2 acts on the shaft 3 in a direction opposite to the axial force F1 (toward the distal side) via the drive rod 33, the first gripping piece 16, and the support pin 19.

In this modification, when the operation force is applied to the handle 21 and the gripping pieces 16 and 17 are thereby closed against the bias of the biasing member 37, the shaft 3 moves (for a small movement), under the axial force F1, from the state in which the recess opposing surface (second contact surface) 48 abuts on the protrusion opposing surface 46 of the housing 2, toward the proximal side with respect to the housing 2. As a result, in the closed state of the gripping pieces 16 and 17 the recess opposing surface (first contact surface) 47 of the shaft 3 abuts on the protrusion opposing surface (first receiving surface) 45 of the housing 2.

In the same manner as in the first embodiment, when the recess opposing surface (first contact surface) 47 abuts on the protrusion opposing surface (first receiving surface) 45 in this modification, the pressing force (first pressing force) P1 acts from the recess opposing surface 47 of the shaft 3 onto the protrusion opposing surface 45 of the housing 2, and the rotation sliding resistance (first rotation sliding resistance) γ1 is produced between the recess opposing surface (first contact surface) 47 of the shaft 3 and the housing 2 around the reference rotation axis R. In this modification, with the axial force F1 being larger than the axial force F2, the pressing force (first pressing force) P1 is larger than the pressing force (second pressing force) P2, and the rotation sliding resistance (first rotation sliding resistance) γ1 is larger than the aforementioned rotation sliding resistance (second rotation sliding resistance) γ2.

With the rotation sliding resistance γ1 being large, when the gripping pieces 16 and 17 are closed and the recess opposing surface (first contact surface) 47 abuts on the protrusion opposing surface (first receiving surface) 45, the movement of the engagement recess 42 around the reference rotation axis R with respect to the engagement protrusion 41 is regulated by the rotation sliding resistance (first rotation sliding resistance) γ1 in this modification. The rotation of the shaft 3 and the end effector 5 around the reference rotation axis R with respect to the housing 2 is thereby suppressed. Therefore, when the recess opposing surface 47 abuts on the protrusion opposing surface 45 of the housing 2, the rotation of the shaft 3 around the reference rotation axis R caused by the force acting on the end effector 5 is suppressed. In this modification, the same function and effects as in the first embodiment are exhibited.

As in the tenth modification in which the shaft 3 extends through the inside of the drive rod 33, which is the open/close drive member, modifications may be made to the configuration based on any of the first to ninth modifications.

Figure 21:
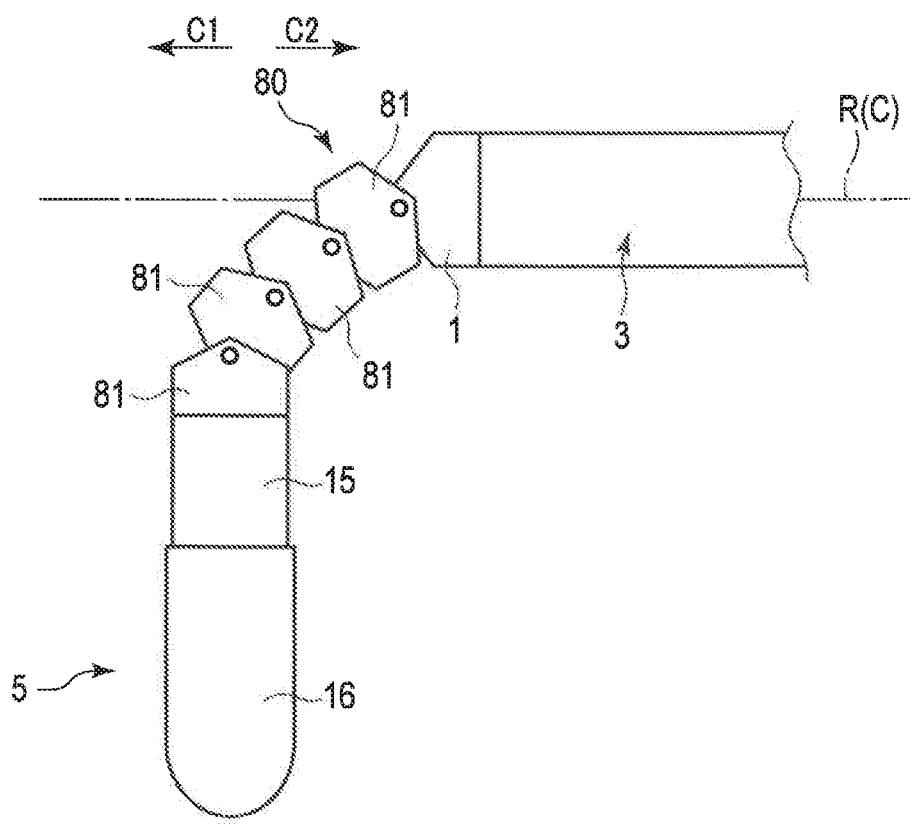
FIG. 21 is a schematic diagram showing the configuration of the distal portion of the treatment instrument according to an eleventh modification.

Furthermore, the treatment instrument in which a rotation moment is produced around the reference rotation axis R by the force acting on the end effector 5 is not limited to the treatment instrument 1 provided with the bending joint 18 as in the above-mentioned embodiment. For example, in the eleventh modification, a curving section 80 may be provided in place of the bending joint 18 on the distal side with respect to the shaft 3, as illustrated in FIG. 21. In the curving section 80, a plurality of curve pieces 81 are aligned, and each of the curve pieces 81 is pivotally coupled to adjacent curve piece/pieces (corresponding one or two of the curve pieces 81). In place of the bend dial (bending operation input member) 23, a curving operation input member is provided in the housing 2, and when an operation is input from the curving operation input section, an operation force is transmitted to a curving drive member (not shown) such as a wire or flat springs. With the operation force transmitted to the curving drive member, the curving drive member moves along the reference rotational axis R. As a result, the curving section 80 is actuated and the end effector 5 including the curve section 80 curves with respect to the shaft 3 (reference rotation axis R).

When a force acts on the end effector 5 that is in the state of being curved with respect to the shaft 3, the force acts on a position away from the reference rotation axis R as described above. This may cause a rotation moment around the reference rotation axis R (around the center axis of the shaft 3). In this modification, even if a rotation moment appears around the reference rotation axis R due to the force acting on the end effector 5, the rotation of the end effector 5 and the shaft 3 around the reference rotation axis R in the state of the gripping pieces 16 and 17 being closed can effectively be prevented by adopting the same configuration as the above-mentioned embodiment.

Figure 22:
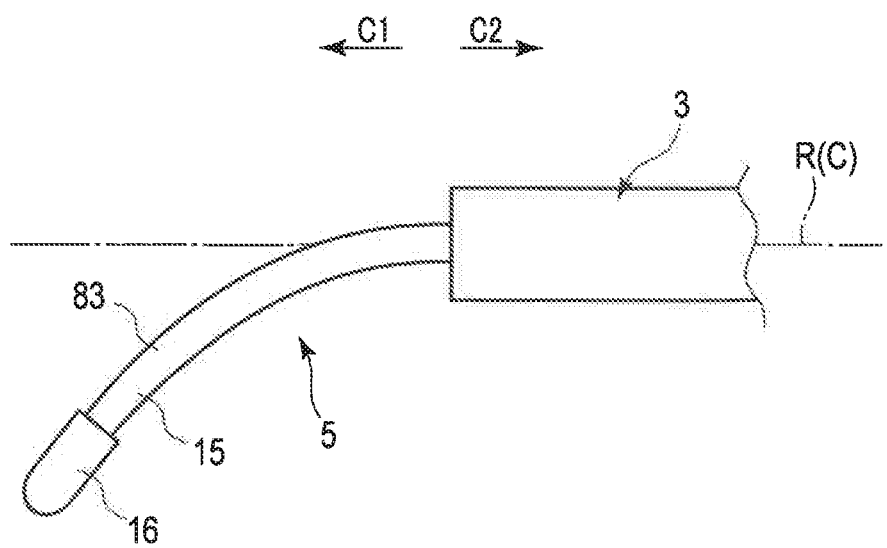
FIG. 22 is a schematic diagram showing the configuration of the distal portion of the treatment instrument according to a twelfth modification.

In the twelfth modification shown in FIG. 22, the end effector 5 protrudes from the distal end of the shaft 3 toward the distal side, and the end effector 5 is provided with a curved extension portion 83 that extends in a curved state with respect to the shaft 3 (reference rotation axis R). In this modification, the force acts on the end effector 5 including the gripping pieces 16 and 17 at a position located on the distal side with respect to the curved extension portion 83. As the result, because the force is applied to a position away from the reference rotation axis R, a rotation moment may be produced around the reference rotation axis R (around the center axis of the shaft 3). In this modification, even if a rotation moment appears around the reference rotation axis R due to the force acting on the end effector 5, the rotation of the end effector 5 and the shaft 3 around the reference rotation axis R in the state of the gripping pieces 16 and 17 being closed can be effectively prevented by adopting the same configuration as the above-mentioned embodiment.

In the above described embodiment, the end effector (5) of the treatment instrument (1) comprises the first gripping piece (16) and the second gripping piece (17), and the first gripping piece (16) and the second gripping piece (17) can be opened and closed with respect to each other. The treatment instrument (1) comprises a housing (2) that can be held, a supporter (19) pivotally supporting the first gripping piece (16), and a shaft (3) that is rotatable together with the end effector (5) and the supporter (19) around a reference rotation axis (R) with respect to the housing (2). A drive member (33) is connected to the first gripping piece (16), and with the drive member (33) moving along the reference rotation axis (R), the first gripping piece (16) pivots around the supporter (19). When the first gripping piece (15) and the second gripping piece (17) are closed in accordance with the pivoting of the first gripping piece (16), the first axial force (F1; F3) acts on the shaft (3) via the first gripping piece (16) and the first axis (19) in a direction along the reference rotation axis (R). With the shaft (3) moving along the reference rotation axis (R) with respect to the housing (2) under the first axial force (F1; F3), the first contact surface (47; 48; 65; 66; 73) abuts on the housing (2), and the rotation of the shaft (3) around the reference rotation axis (R) with respect to the housing (2) is thereby suppressed.

Reference Examples

In addition to the configurations described above, the following configuration may be adopted in the reference examples described below. In the first reference example shown in FIGS. 23 and 24, a gear 91 is fixed to the shaft 3, and an engagement piece 92 is provided in the handle 21. The gear 91 is rotatable together with the shaft 3, the end effector 5, and the movable member 31 around the reference rotation axis R with respect to the housing 2 and the handle 21. Furthermore, the engagement piece 92 pivots together with the handle 21, with respect to the housing 2. In this reference example, by closing the handle 21 with respect to the grip 12 against the bias of the biasing member 37, the movable member 31 and the drive rod (open/close drive member) 33 move toward the proximal side, thereby closing the gripping pieces 16 and 17 with respect to each other. In addition, in this reference example, when the handle 21 is closed with respect to the grip 12, the engagement piece 92 comes to engage with the gear 91. With the engagement piece 92 engaged with the gear 91, the rotation of the shaft 3 and the end effector 5 around the reference rotation axis R with respect to the handle 21 is suppressed.

In this reference example, in the closed state of the gripping pieces 16 and 17, the rotation of the shaft 3 and the end effector 5 around the reference rotation axis R with respect to the housing 2 is suppressed under the rotation sliding resistance (first rotation sliding resistance) γ1 between the recess opposing surface 47 of the shaft 3 and the housing 2. In addition, the rotation of the shaft 3 and the end effector 5 around the reference rotation axis R is suppressed by the engagement of the engagement piece 92 with the gear 91. Thus, in the state of the gripping pieces 16 and 17 being closed, the suppression of the rotation of the shaft 3 around the reference rotation axis R that is caused by the force acting on the end effector 5 can be further enhanced.

Figure 25:
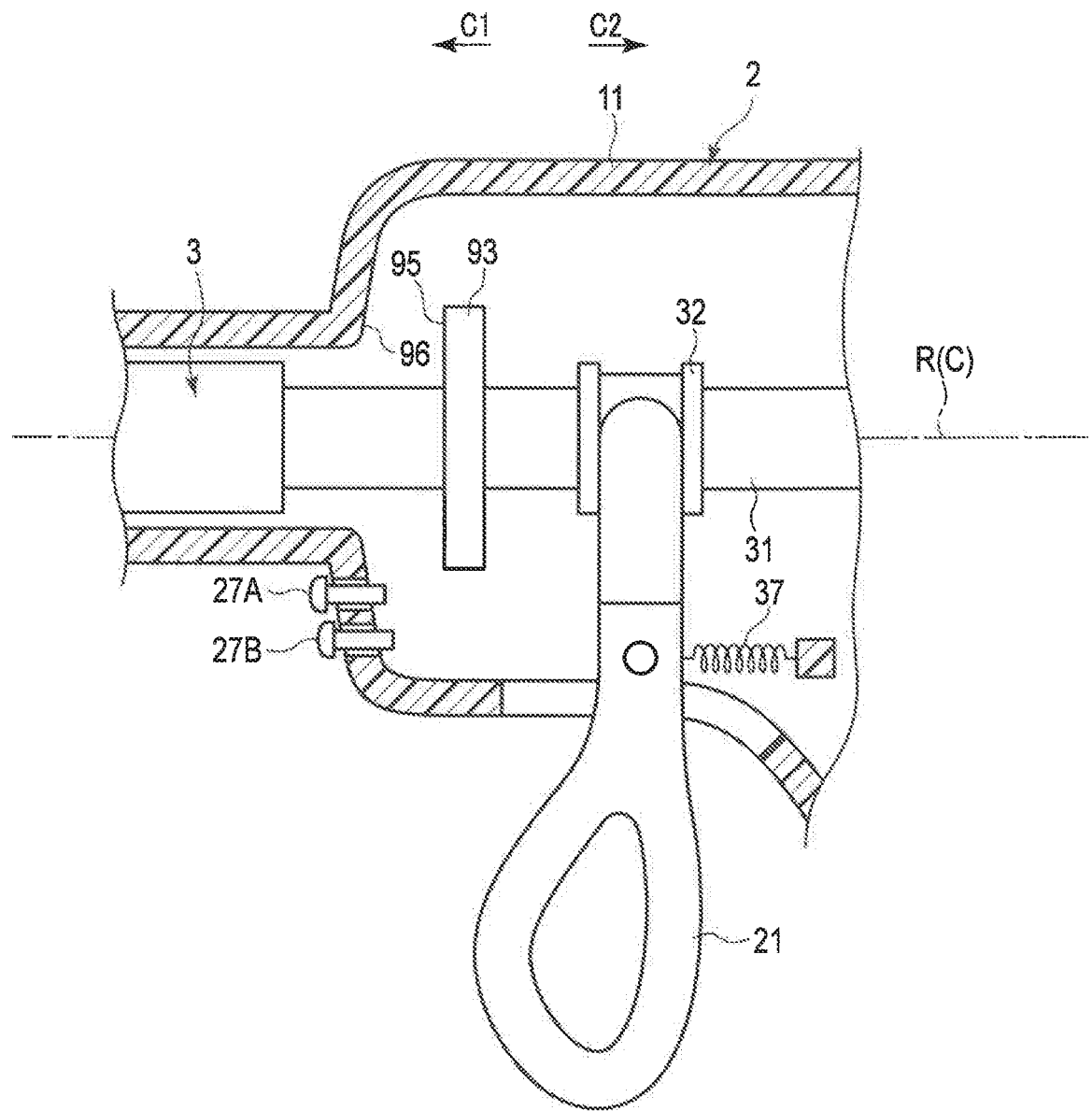
FIG. 25 is a schematic diagram showing the internal configuration of the housing according to a second reference example.

In the second reference example shown in FIG. 25, the movable member 31 is provided with a contact surface 95 which faces toward the distal side, and the housing 2 is provided with a reception surface 96 which faces toward the proximal side. The contact surface 95 and the reception surface 96 are arranged to be opposed to each other. The contact surface 95 is movable together with the movable member 31 along the reference rotation axis R with respect to the housing 2. When the gripping pieces 16 and 17 are open, the contact surface 95 is positioned on the proximal side away from the reception surface 96 so as not to be in contact with the reception surface 96. In this reference example, when the handle 21 is closed with respect to the grip 12 against the bias of the biasing member 37, the movable member 31 and the drive rod (open/close drive member) 33 move toward the distal side, thereby closing the gripping pieces 16 and 17 with respect to each other. Here, the contact surface 95 also moves, together with the movable member 31 and the drive rod 33, toward the distal side. As a result, the contact surface 95 abuts on (comes to engage with) the reception surface 96. With the contact surface 95 abutting on the reception surface 96, friction is produced between the contact surface 95 and the reception surface 96, which suppresses the rotation of the movable member 31, the drive rod 33, the shaft 3 and the end effector 5 around the rotation axis R with respect to the handle 21.

Therefore, in the present reference example, in the closed state of the gripping pieces 16 and 17, the rotation of the shaft 3 and the end effector 5 around the reference rotation axis R with respect to the housing 2 can be suppressed by the rotation sliding resistance (first rotation sliding resistance) γ1, for example, between the recess opposing surface 47 of the shaft 3 and the housing 2. At the same time, the rotation of the shaft 3 and the end effector 5 around the reference rotation axis R can be suppressed by the friction (rotation friction resistance) between the contact surface 95 of the movable member 31 and the housing 2. Therefore, in the state of the gripping pieces 16 and 17 being closed, the suppression of the rotation of the shaft 3 around the reference rotation axis R caused by the force acting on the end effector 5 can be further enhanced.

In the second reference example, at least one of the contact surface 95 and the reception surface 96 may be formed into a serrated surface. With such an arrangement, the frictional force between the contact surface 95 of the movable member 31 and the reception surface 96 of the housing 2 increases in the closed state of the gripping pieces 16 and 17. The suppression of the rotation of the shaft 3 around the reference rotation axis R, which is caused by the force acting on the end effector 5, thereby can be further enhanced. In another reference example, a contact surface (not shown) may be provided on the drive rod 33 in place of the contact surface 95, and a reception surface (not shown), on which this contact surface can abut, may be provided in the housing 2. In this case also, the contact surface of the drive rod 33 abuts on the reception surface of the housing 2 in the closed state of the gripping pieces 16 and 17. As a result, in a manner similar to the second reference example, the friction between the contact surface and the reception surface suppresses the rotation of the movable member 31, the drive rod 33, the shaft 3, and the end effector 5 around the reference rotation axis R with respect to the handle 21.

In one reference example, in the configuration in which the drive rod (open/close drive member) 33 moves toward the proximal side to close the gripping pieces 16 and 17 as in the first embodiment, the contact surface (95) of the movable member 31 or the drive rod 33 may be configured to abut on the reception surface (96) of the housing 2 as in the second reference example. In another reference example, in the configuration in which the shaft 3 extends through the inside of the drive rod 33 as in the tenth modification, the contact surface (95) of the movable member 31 or the drive rod 33 may be configured to abut on the reception surface (96) of the housing 2, as in the second reference example. In each of these reference examples, the contact surface (95) of the movable member 31 or the drive rod 33 abuts on the reception surface (96) of the housing 2 in the closed state of the gripping pieces 16 and 17. In the same manner as in the second reference example, the rotation of the movable member 31, the drive rod 33, the shaft 3, and the end effector 5 around the reference rotation axis R with respect to the handle 21 can be suppressed by the friction between the contact surface (95) and the reception surface (96).

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment instrument, comprising:
   an end effector including a first jaw, a second jaw, and a supporter, the supporter pivotally supporting the first jaw, and the first jaw and the second jaw being opened or closed with respect to each other in accordance with pivoting of the first jaw around the supporter with respect to the supporter;
   an elongated member having a longitudinal axis, the end effector being attached at a distal end of the elongated member;
   a housing including an operation input member, an operation of opening or closing the end effector being input with the operation input member, and the elongated member being attached to the housing in a state in which the elongated member is rotatable together with the end effector around the longitudinal axis;
   a drive member having a distal end connected to the first jaw, the drive member being configured to move along the longitudinal axis of the elongated member based on the operation input with the operation input member so that the first jaw pivots around the supporter, and thereby being configured to close the first jaw and the second jaw with respect to each other in accordance with the pivoting of the first jaw so that the drive member applies a first axial force onto the elongated member by way of the first jaw and the supporter in a direction along the longitudinal axis;
   a first contact surface provided on the elongated member, the first contact surface being configured to abut on the housing when the elongated member moves along the longitudinal axis with respect to the housing under the first axial force, thereby suppressing rotation of the elongated member around the longitudinal axis with respect to the housing; and
   a biasing member configured to urge the drive member into an open state of the first jaw and the second jaw, thereby applying a second axial force on the elongated member in a direction opposite to the first axial force by way of the drive member, the first jaw, and the supporter.

2. The treatment instrument, according to claim 1, wherein
   the elongated member includes a second contact surface configured to abut on the housing by action of the second axial force from the biasing member, in the open state of the first jaw and the second jaw.

3. The treatment instrument according to claim 2, wherein
   rotation sliding resistance between the first contact surface and the housing in a state of the first contact surface abutting on the housing is greater than rotation sliding resistance between the second contact surface and the housing in a state of the second contact surface abutting on the housing.

4. The treatment instrument according to claim 3, wherein
   a pressing force of the first contact surface to the housing in the state of the first contact surface abutting on the housing is greater than a pressing force of the second contact surface to the housing in the state of the second contact surface abutting on the housing.

5. The treatment instrument according to claim 2, wherein
   the operation input member is configured to move the drive member against bias from the biasing member under application of an operation force, thereby closing the first jaw and the second jaw with respect to each other, and
   when the first jaw and the second jaw are closed under the application of the operation force in the operation input member, the first axial force greater than the second axial force acts on the elongated member by way of the drive member, the first jaw, and the supporter, and thereby the elongated member moves from a state of the second contact surface abutting on the housing, to a direction toward which the first axial force acts with respect to the housing.

6. The treatment instrument according to claim 2, wherein
   the elongated member includes a rotational operation input member that is rotatable around the longitudinal axis with respect to the housing, the first contact surface and the second contact surface being provided in the rotational operation input member.

7. The treatment instrument according to claim 2, wherein the first contact surface extends in a direction intersecting with the longitudinal axis.

8. The treatment instrument according to claim 7, wherein the second contact surface extends in the direction intersecting with the longitudinal axis, the second contact surface being opposed to the first contact surface.

9. The treatment instrument according to claim 1, wherein the end effector is bendable or curve able with respect to the elongated member.

10. The treatment instrument according to claim 1, wherein
the elongated member includes a rotational operation input member that is rotatable around the longitudinal axis with respect to the housing, the first contact surface being provided in the rotational operation input member.

11. The treatment instrument according to claim 1, wherein
the first contact surface extends in a direction intersecting with the longitudinal axis.

* * * * *